(12) United States Patent
Foster et al.

(10) Patent No.: US 7,644,458 B2
(45) Date of Patent: *Jan. 12, 2010

(54) HOSPITAL BED

(75) Inventors: L. Dale Foster, Little Torch Key, FL (US); Ryan Anthony Reeder, Carmel, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 432 days.

This patent is subject to a terminal disclaimer.

(21) Appl. No.: 11/625,512

(22) Filed: Jan. 22, 2007

(65) Prior Publication Data

US 2007/0113342 A1 May 24, 2007

Related U.S. Application Data

(60) Continuation of application No. 11/322,747, filed on Dec. 30, 2005, now abandoned, which is a continuation of application No. 10/832,599, filed on Apr. 27, 2004, now Pat. No. 6,993,799, which is a continuation of application No. 10/195,981, filed on Jul. 16, 2002, now Pat. No. 6,725,474, which is a continuation of application No. 10/085,855, filed on Feb. 28, 2002, now Pat. No. 6,694,548, which is a continuation of application No. 09/655,525, filed on Sep. 5, 2000, now Pat. No. 6,374,436, which is a continuation of application No. 09/370,272, filed on Aug. 9, 1999, now Pat. No. 6,112,345, which is a division of application No. 09/009,522, filed on Jan. 20, 1998, now Pat. No. 5,933,888, which is a division of application No. 08/755,480, filed on Nov. 22, 1996, now Pat. No. 5,708,997, which is a division of application No. 08/277,243, filed on Jul. 19, 1994, now Pat. No. 5,577,279, which is a continuation-in-part of application No. 08/234,403, filed on Apr. 28, 1994, now Pat. No. 5,454,126, and a continuation-in-part of application No. 08/230,061, filed on Apr. 21, 1994, now Pat. No. 5,513,406, which is a continuation-in-part of application No. 08/186,657, filed on Jan. 25, 1994, now Pat. No. 5,479,666.

(51) Int. Cl.
*A61G 7/08* (2006.01)
*B62D 51/04* (2006.01)

(52) U.S. Cl. ............................. 5/510; 5/86.1; 180/19.3

(58) Field of Classification Search ..................... 5/510, 5/86.1; 180/11, 15, 19.3
See application file for complete search history.

(56) References Cited

U.S. PATENT DOCUMENTS

| 813,213 | A | 2/1906 | Johnson |
| 1,290,809 | A | 1/1919 | Truax |
| 1,398,203 | A | 11/1921 | Schmidt |
| 1,598,124 | A | 8/1926 | Evans |

(Continued)

FOREIGN PATENT DOCUMENTS

BE    1007895 A3    11/1995

(Continued)

*Primary Examiner*—Michael Trettel
(74) *Attorney, Agent, or Firm*—Barnes & Thornburg LLP

(57) ABSTRACT

A patient support apparatus including a patient support and a powered transport device to facilitate movement of a patient support.

20 Claims, 14 Drawing Sheets

U.S. PATENT DOCUMENTS

| | | | |
|---|---|---|---|
| 1,992,262 A | 2/1935 | Upp |
| 2,039,901 A | 5/1936 | Hawley |
| 2,308,592 A | 1/1943 | Drexler et al. |
| 2,470,524 A | 5/1949 | Scudder |
| 2,564,083 A | 8/1951 | Stechert |
| 2,599,717 A | 6/1952 | Menzies |
| 2,607,929 A | 8/1952 | Balluff |
| 2,635,899 A | 4/1953 | Osbon, Jr. |
| 2,673,771 A | 3/1954 | Krewson |
| 2,696,963 A | 12/1954 | Shepherd |
| 2,847,006 A | 8/1958 | Griffith |
| 2,978,053 A | 4/1961 | Schmidt |
| 2,999,555 A | 9/1961 | Stroud et al. |
| 3,010,121 A | 11/1961 | Breach |
| 3,032,059 A | 5/1962 | McLeod |
| 3,038,174 A | 6/1962 | Brown et al. |
| 3,041,636 A | 7/1962 | Twedt |
| 3,112,001 A | 11/1963 | Wise |
| 3,191,990 A | 6/1965 | Rugs et al. |
| 3,210,779 A | 10/1965 | Herbold |
| 3,220,021 A | 11/1965 | Nelson |
| 3,220,022 A | 11/1965 | Nelson |
| 3,262,133 A | 7/1966 | Beitzel |
| 3,281,103 A | 10/1966 | Kisling |
| 3,281,141 A | 10/1966 | Smiley et al. |
| 3,304,116 A | 2/1967 | Stryker |
| 3,305,876 A | 2/1967 | Hutt |
| 3,362,704 A | 1/1968 | Pilz |
| 3,380,546 A | 4/1968 | Rabjohn |
| 3,404,746 A | 10/1968 | Slay |
| 3,406,772 A | 10/1968 | Ahrent et al. |
| 3,452,371 A | 7/1969 | Hirsch |
| 3,524,512 A | 8/1970 | Voeks et al. |
| 3,544,127 A | 12/1970 | Dobson |
| 3,593,350 A | 7/1971 | Knight et al. |
| 3,596,725 A | 8/1971 | Horns |
| 3,618,966 A | 11/1971 | Vandervest |
| 3,680,880 A | 8/1972 | Blaauw |
| 3,686,696 A | 8/1972 | Lanigan |
| 3,757,355 A | 9/1973 | Allen et al. |
| 3,795,284 A | 3/1974 | Mracek et al. |
| 3,802,524 A | 4/1974 | Seidel |
| 3,814,199 A | 6/1974 | Jones |
| 3,876,018 A | 4/1975 | Mracek et al. |
| 3,876,024 A | 4/1975 | Shieman et al. |
| 3,898,702 A | 8/1975 | Goodman |
| 3,938,608 A | 2/1976 | Folco-Zambelli |
| 3,948,344 A | 4/1976 | Johnson et al. |
| 4,006,789 A | 2/1977 | Stultz et al. |
| 4,033,420 A | 7/1977 | De Masters |
| 4,137,984 A | 2/1979 | Jennings et al. |
| 4,139,917 A | 2/1979 | Fenwick |
| 4,155,421 A | 5/1979 | Johnson et al. |
| 4,183,109 A | 1/1980 | Howell |
| 4,221,273 A | 9/1980 | Finden |
| 4,225,104 A | 9/1980 | Larson |
| 4,225,989 A | 10/1980 | Corbett et al. |
| 4,227,269 A | 10/1980 | Johnston |
| 4,247,091 A | 1/1981 | Glowacki et al. |
| 4,251,105 A | 2/1981 | Barker |
| 4,258,445 A | 3/1981 | Zur |
| 4,262,872 A | 4/1981 | Kodet |
| 4,270,233 A | 6/1981 | Mulligan |
| 4,272,856 A | 6/1981 | Wegener et al. |
| 4,274,503 A | 6/1981 | Mackintosh |
| 4,277,100 A | 7/1981 | Beougher |
| 4,281,730 A | 8/1981 | Swersey et al. |
| D260,816 S | 9/1981 | Zissimopoulos et al. |
| 4,298,083 A | 11/1981 | Johnson et al. |
| 4,352,991 A | 10/1982 | Kaufman |
| 4,375,707 A | 3/1983 | Boerigter |
| 4,399,885 A | 8/1983 | Johnson et al. |
| 4,411,035 A | 10/1983 | Fenwick |
| 4,415,049 A | 11/1983 | Wereb |
| 4,417,638 A | 11/1983 | Harvey |
| 4,417,639 A | 11/1983 | Wegener |
| 4,420,052 A | 12/1983 | Hale |
| 4,435,864 A | 3/1984 | Callaway |
| 4,475,611 A | 10/1984 | Fisher |
| 4,475,613 A | 10/1984 | Walker |
| 4,482,783 A | 11/1984 | Laimins |
| 4,487,276 A | 12/1984 | Swersey et al. |
| 4,511,158 A | 4/1985 | Varga et al. |
| 4,517,690 A | 5/1985 | Wegener |
| 4,528,704 A | 7/1985 | Wegener et al. |
| 4,566,707 A | 1/1986 | Nitzberg |
| 4,567,957 A | 2/1986 | Johnson |
| 4,571,759 A | 2/1986 | Sasaki et al. |
| 4,578,833 A | 4/1986 | Vrzalik |
| 4,584,989 A | 4/1986 | Stith |
| 4,592,104 A | 6/1986 | Foster et al. |
| 4,600,209 A | 7/1986 | Kerr, Jr. |
| 4,614,246 A | 9/1986 | Masse et al. |
| 4,615,058 A | 10/1986 | Feldt |
| 4,627,426 A | 12/1986 | Wegener et al. |
| 4,639,954 A | 2/1987 | Speed |
| 4,646,860 A | 3/1987 | Owens et al. |
| 4,686,719 A | 8/1987 | Johnson et al. |
| 4,691,397 A | 9/1987 | Netzer |
| 4,729,576 A | 3/1988 | Roach |
| 4,751,754 A | 6/1988 | Bailey et al. |
| 4,759,418 A | 7/1988 | Goldenfeld et al. |
| 4,768,241 A | 9/1988 | Beney |
| 4,787,104 A | 11/1988 | Grantham |
| 4,793,428 A | 12/1988 | Swersey |
| 4,795,122 A | 1/1989 | Petre |
| 4,796,313 A | 1/1989 | DiMatteo et al. |
| 4,805,249 A | 2/1989 | Usman et al. |
| 4,811,988 A | 3/1989 | Immel |
| 4,821,348 A | 4/1989 | Pauna |
| 4,848,504 A | 7/1989 | Olson |
| 4,856,123 A | 8/1989 | Henderson et al. |
| 4,862,529 A | 9/1989 | Peck |
| 4,874,055 A | 10/1989 | Beer |
| 4,887,325 A | 12/1989 | Tesch |
| 4,894,876 A | 1/1990 | Fenwick |
| 4,896,389 A | 1/1990 | Chamberland |
| 4,905,944 A | 3/1990 | Jost et al. |
| 4,920,587 A | 5/1990 | Kerr |
| 4,944,292 A | 7/1990 | Gaeke et al. |
| 4,945,592 A | 8/1990 | Sims et al. |
| 4,949,413 A | 8/1990 | Goodwin |
| 4,953,243 A | 9/1990 | Birkmann |
| 4,953,247 A | 9/1990 | Hasty |
| 4,957,121 A | 9/1990 | Icenogle et al. |
| 4,962,552 A | 10/1990 | Hasty |
| 4,966,340 A | 10/1990 | Hunter |
| 4,979,582 A | 12/1990 | Forster |
| 4,981,309 A | 1/1991 | Froeschle et al. |
| 4,985,946 A | 1/1991 | Foster et al. |
| 4,987,620 A | 1/1991 | Sharon |
| 5,005,230 A | 4/1991 | Congdon |
| 5,022,105 A | 6/1991 | Catoe |
| 5,033,563 A | 7/1991 | Brainerd, Jr. et al. |
| 5,042,470 A | 8/1991 | Kanesaka |
| 5,044,029 A | 9/1991 | Vrzalik |
| 5,050,695 A | 9/1991 | Kleinwolterink, Jr. |
| 5,054,141 A | 10/1991 | Foster et al. |
| 5,060,327 A | 10/1991 | Celestina et al. |
| 5,060,959 A | 10/1991 | Davis et al. |
| 5,065,464 A | 11/1991 | Blanchard et al. |
| 5,067,189 A | 11/1991 | Weedling et al. |
| 5,072,463 A | 12/1991 | Willis |
| 5,072,906 A | 12/1991 | Foster |

| | | | | | |
|---|---|---|---|---|---|
| 5,077,843 | A | 1/1992 | Foster et al. | | |
| 5,083,331 | A | 1/1992 | Schnelle et al. | 6,993,799 B2 | 2/2006 Foster et al. |
| 5,083,625 | A | 1/1992 | Bleicher | FOREIGN PATENT DOCUMENTS | |
| 5,084,922 | A | 2/1992 | Louit | | |
| 5,090,077 | A | 2/1992 | Caden et al. | CA 2010543 | 9/1990 |
| 5,092,007 | A | 3/1992 | Hasty | DE 716 981 | 2/1942 |
| 5,094,314 | A | 3/1992 | Hayata | DE 595 097 | 9/1977 |
| 5,095,561 | A | 3/1992 | Green et al. | DE 2 818 189 | 6/1979 |
| 5,103,518 | A | 4/1992 | Gilroy et al. | DE 2 812 037 | 9/1979 |
| 5,103,519 | A | 4/1992 | Hasty | DE 3 915 882 | 11/1990 |
| 5,109,560 | A | 5/1992 | Uetake | DE 295 18 502 | 1/1997 |
| 5,117,521 | A | 6/1992 | Foster et al. | DE 199 21 503 | 4/2000 |
| 5,117,819 | A | 6/1992 | Servidio et al. | EP 0 062 180 | 10/1982 |
| 5,121,512 | A | 6/1992 | Kaufmann | EP 0 093 700 | 11/1983 |
| 5,121,806 | A | 6/1992 | Johnson | EP 0 178 951 | 4/1986 |
| 5,129,117 | A | 7/1992 | Celestina et al. | EP 0 329 504 | 8/1989 |
| 5,134,737 | A | 8/1992 | Wyman | EP 0 352 647 | 1/1990 |
| 5,156,226 | A | 10/1992 | Boyer et al. | EP 0 403 202 | 12/1990 |
| 5,157,800 | A | 10/1992 | Borders | EP 0 420 263 | 12/1990 |
| 5,181,289 | A | 1/1993 | Kassai | FR 2 285 113 | 4/1976 |
| 5,193,633 | A | 3/1993 | Bzenwa | GB 415450 | 8/1934 |
| 5,201,819 | A | 4/1993 | Shiraishi et al. | GB 995235 | 6/1965 |
| 5,222,567 | A | 6/1993 | Broadhead et al. | GB 2153771 | 8/1985 |
| 5,279,010 | A | 1/1994 | Ferrand et al. | JP 46-31490 | 9/1971 |
| 5,293,950 | A | 3/1994 | Marliac | JP 47-814 | 8/1972 |
| 5,319,813 | A | 6/1994 | DiMatteo et al. | JP 48-44792 | 6/1973 |
| 5,335,651 | A | 8/1994 | Foster et al. | JP 48-44793 | 6/1973 |
| 5,337,845 | A | 8/1994 | Foster et al. | JP 48-54494 | 7/1973 |
| 5,342,114 | A | 8/1994 | Burke et al. | JP 48-54495 | 7/1973 |
| 5,348,326 | A | 9/1994 | Fullenkamp et al. | JP 49-29855 | 8/1974 |
| 5,358,265 | A | 10/1994 | Yaple | JP 51-20491 | 8/1974 |
| 5,370,111 | A | 12/1994 | Reeder et al. | JP 53-9091 | 1/1978 |
| 5,384,927 | A | 1/1995 | Mardero et al. | JP 53-96397 | 8/1978 |
| 5,398,357 | A | 3/1995 | Foster et al. | JP 56-68523 | 6/1981 |
| 5,447,317 | A | 9/1995 | Gehlsen et al. | JP 56-68524 | 6/1981 |
| 5,454,126 | A | 10/1995 | Foster et al. | JP 56-73822 | 6/1981 |
| 5,457,831 | A | 10/1995 | Foster et al. | JP 57-157325 | 9/1982 |
| 5,477,100 | A | 12/1995 | Kataoka | JP 57-187521 | 11/1982 |
| 5,477,935 | A | 12/1995 | Chen | JP 59-37946 | 3/1984 |
| 5,479,666 | A | 1/1996 | Foster et al. | JP 59-183756 | 10/1984 |
| 5,483,709 | A | 1/1996 | Foster et al. | JP 59-186554 | 10/1984 |
| 5,495,904 | A | 3/1996 | Zwaan et al. | JP 60-12058 | 1/1985 |
| 5,513,406 | A | 5/1996 | Foster et al. | JP 60-12059 | 1/1985 |
| 5,537,701 | A | 7/1996 | Elliott | JP 0-31751 | 2/1985 |
| 5,542,690 | A | 8/1996 | Kozicki | JP 60-21751 | 2/1985 |
| 5,577,279 | A | 11/1996 | Foster et al. | JP 60-31749 | 2/1985 |
| 5,580,207 | A | 12/1996 | Kiebooms et al. | JP 60-31750 | 2/1985 |
| 5,672,849 | A | 9/1997 | Foster et al. | JP 60-122561 | 7/1985 |
| 5,708,997 | A | 1/1998 | Foster et al. | JP 60-188152 | 9/1985 |
| 5,933,888 | A | 8/1999 | Foster et al. | JP 60-188153 | 9/1985 |
| 5,971,091 | A | 10/1999 | Kamen et al. | JP 61-188727 | 8/1986 |
| 6,112,345 | A | 9/2000 | Foster et al. | JP 64-17231 | 1/1989 |
| 6,374,436 | B1 | 4/2002 | Foster et al. | JP 2-84961 | 3/1990 |
| 6,694,548 | B2 | 2/2004 | Foster et al. | JP 4-108525 | 4/1992 |
| 6,725,474 | B2 | 4/2004 | Foster et al. | JP 6-260433 | 9/1994 |
| | | | | WO WO 82/01313 | 4/1982 |
| | | | | WO WO 87/07830 | 12/1987 |

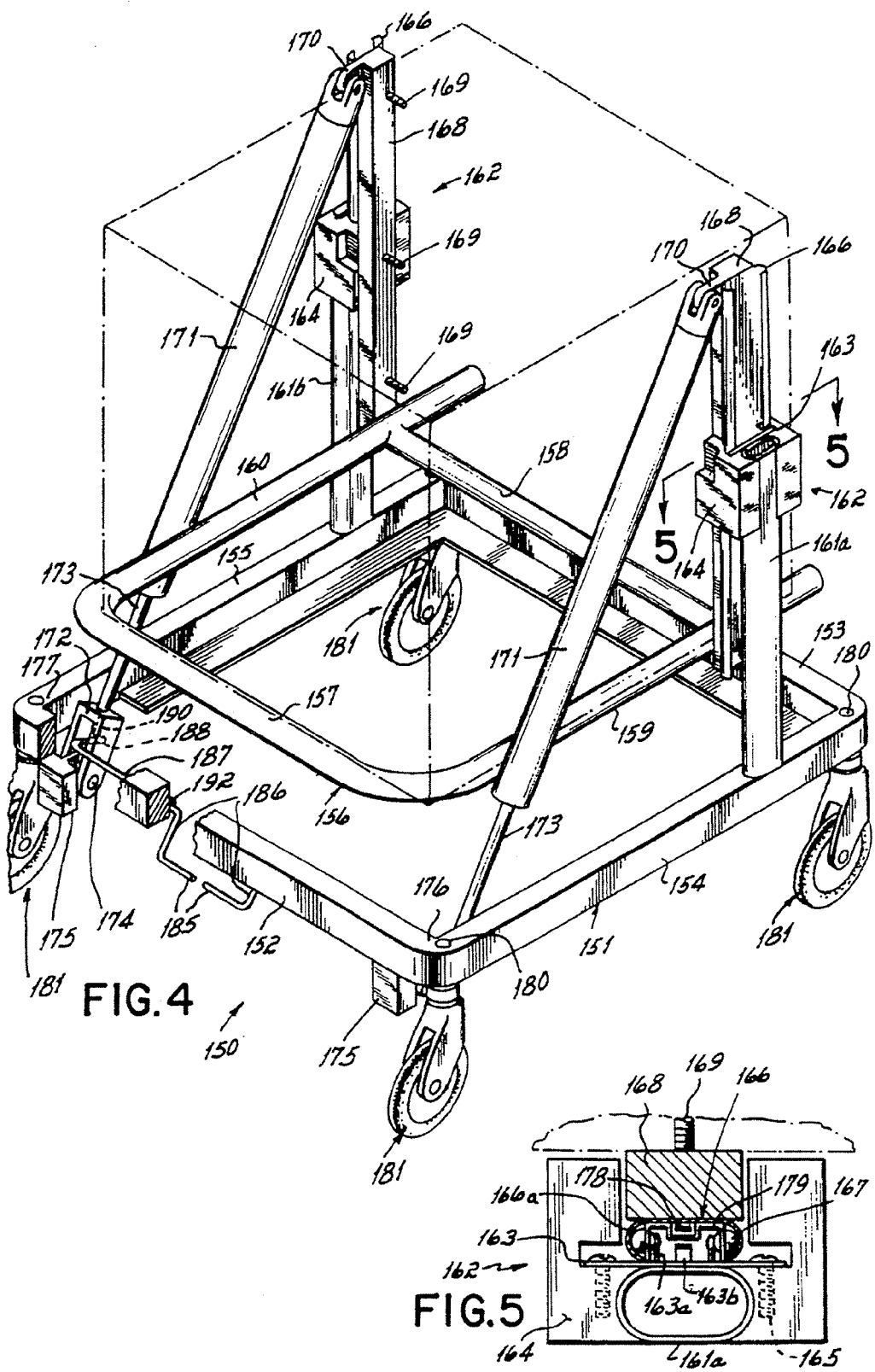

HOSPITAL BED

This application is a continuation of U.S. patent application Ser. No. 11/322,747, filed Dec. 30, 2005 now abandoned, which is a continuation of U.S. patent application Ser. No. 10/832,599, filed Apr. 27, 2004, now U.S. Pat. No. 6,993,799 which is a continuation of U.S. patent application Ser. No. 10/195,981, filed Jul. 16, 2002, now U.S. Pat. No. 6,725,474, which is a continuation of U.S. patent application Ser. No. 10/085,855, filed Feb. 28, 2002, now U.S. Pat. No. 6,694,548, which is a continuation of U.S. patent application Ser. No. 09/655,525, filed Sep. 5, 2000, now U.S. Pat. No. 6,374,436, which is a continuation of U.S. patent application Ser. No. 09/370,272, filed Aug. 9, 1999, now U.S. Pat. No. 6,112,345, which is a divisional of U.S. patent application Ser. No. 09/009,522, filed Jan. 20, 1998, now U.S. Pat. No. 5,933,888, which is a divisional of U.S. patent application Ser. No. 08/755,480, filed Nov. 22, 1996, now U.S. Pat. No. 5,708,997, which is a divisional of U.S. patent application Ser. No. 08/277,243, filed Jul. 19, 1994, now U.S. Pat. No. 5,577,279, which is a continuation in part of U.S. patent application Ser. No. 08/234,403, filed Apr. 28, 1994, now U.S. Pat. No. 5,454,126, which is a continuation in part of U.S. patent application Ser. No. 08/186,657, filed Jan. 25, 1994, now U.S. Pat. No. 5,479,666, and a continuation in part of U.S. patent application Ser. No. 08/230,061, filed Apr. 21, 1994, now U.S. Pat. No. 5,513,406, which is a continuation in part of U.S. patent application Ser. No. 08/186,657, filed Jan. 25, 1994, now U.S. Pat. No. 5,479,666, all of which are hereby incorporated by reference herein as if fully set forth in their entirety. The disclosures of U.S. Pat. Nos. 5,672,849; 5,483,709; 5,337,845; 5,335,651; 5,370,111; and 5,117,521 are hereby incorporated by reference herein as if fully set forth in their entirety.

BACKGROUND AND SUMMARY OF THE INVENTION

This invention relates generally to patient support apparatus, and more particularly to patient support apparatus which include a powered transport device to facilitate movement of a patient support.

According to one aspect of the present invention, a patient support apparatus is provided. The patient support apparatus includes a patient support and a powered transport device. The powered transport device includes a wheel and a motor coupled to the wheel to power rotation of the wheel. The wheel is in contact with the floor to facilitate movement of the patient support when rotated by the motor.

BRIEF DESCRIPTION OF THE DRAWINGS

A detailed description particularly refers to the accompanying figures in which:

FIG. 4 illustrates another embodiment of the ventilator cart of the present disclosure;

FIG. 5 is a view taken along line 5 of FIG. 4;

DETAILED DESCRIPTION OF THE DRAWINGS

Figure 1:
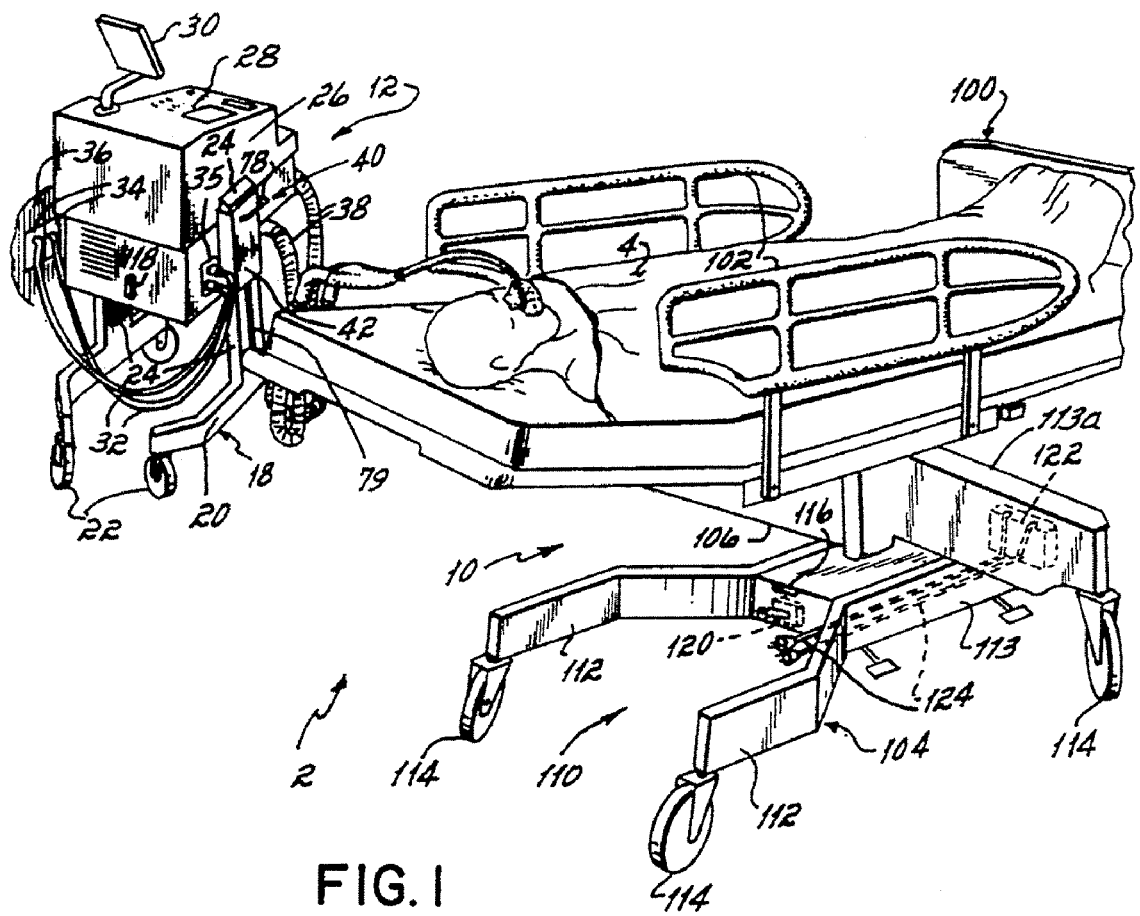
FIG. 1 is a perspective view of the present disclosure with the ventilator in its high position and separated from the hospital bed base and connected to AC wall outlets.
Figure 2:
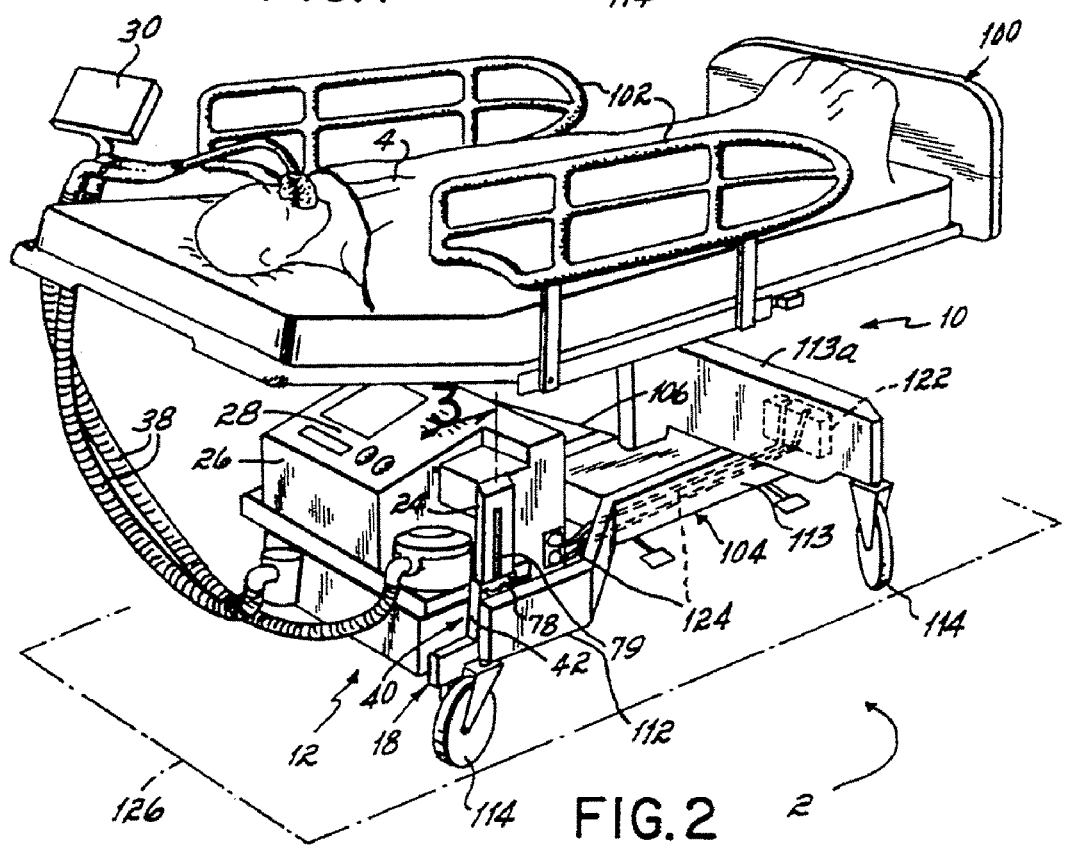
FIG. 2 is a view similar to FIG. 1 but illustrating the ventilator in its low position and docked to the hospital bed base and powered by the bed power supply.

With reference to the drawings, and first to FIGS. 1 and 2, there is illustrated a critical care environment designated generally by the numeral 2 for providing care to a critically ill patient 4. The standard critical care environment 2 includes, generally, a critical care bed assembly 10, and a mobile ventilator assembly 12. Other critical care equipment such as I.V. pumps, various monitors, and one or more terminals for entering patient care data, are also typically present in this environment but are not shown in the drawings for clarity purposes.

The mobile ventilator assembly 12 includes a ventilator cart 18 having a base 20 to which are mounted wheels or casters 22. Extending upwardly from the base 20 are a pair of uprights 24, 24 for supporting a ventilator 26. The ventilator 26 includes a control panel 28 and a flat panel display 30 for monitoring the ventilator 26. The ventilator 26 includes cables 32, 32 to supply power from suitable AC outlets 34, 34 mounted on a wall 36 of a critical care hospital room. The ventilator 26 is tethered to the patient 4 via hoses 38, 38.

Referring to FIG. 1, the ventilator 26 is illustrated in its upwardmost position where it is approximately beside height thereby facilitating operation of the ventilator 26 by a care provider by placing control panel 28 and display 30 at a convenient height.

Figure 3:
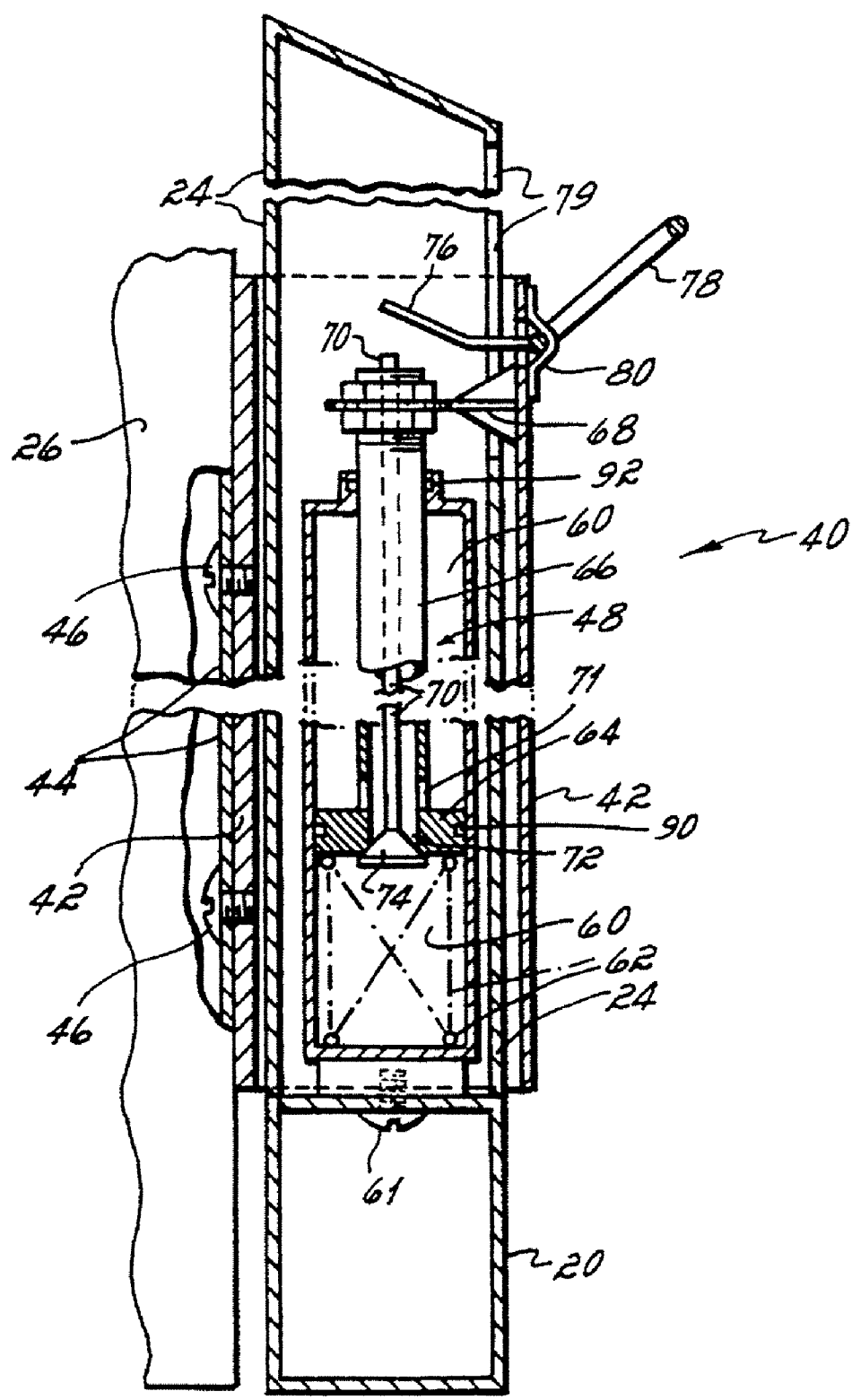
FIG. 3 is a schematic view taken along line 3 of FIG. 2 and illustrating one mechanism for raising and lowering the ventilator on the ventilator cart, the mechanism being shown in a lowered position.
Figure 6:
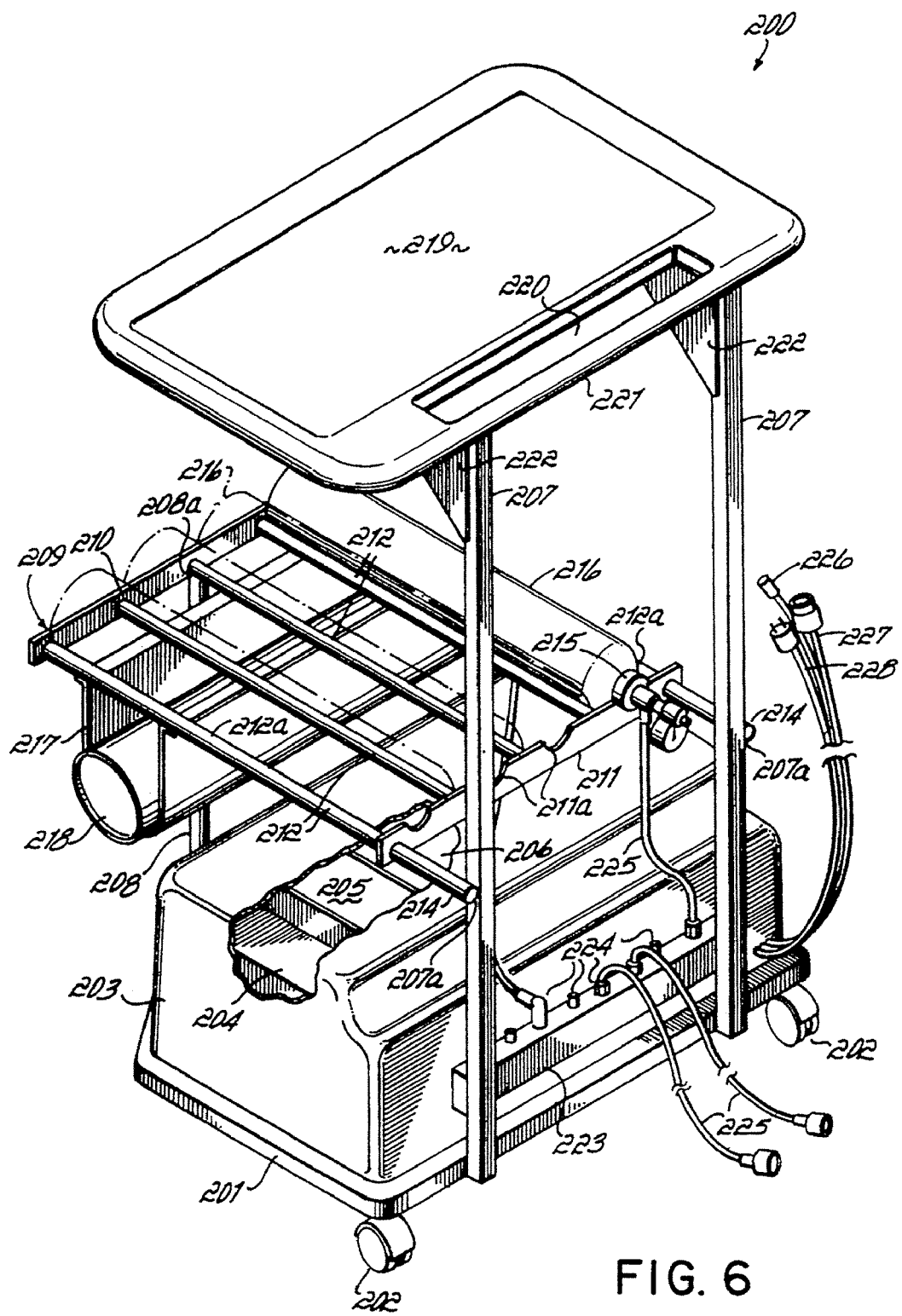
FIG. 6 is a perspective view of the care cart of the present disclosure.

With reference to FIG. 2, it will be noted that the ventilator 26 is lowered and positioned in a downwardmost compact configuration in order to be docked with the critical care bed assembly 10 for transporting both the bed assembly 10 and ventilator assembly 12 as a unit. In order to raise and lower the ventilator 26, each support 24 is provided with an adjusting mechanism 40 which allows for selectively raising and lowering the ventilator 26 on the supports 24. While most any suitable mechanism 40 could be utilized, one such adjusting mechanism 40 is illustrated in FIG. 3. Each mechanism 40 includes a generally box shaped sleeve 42 mounted for vertical sliding movement on its respective support 24. The sleeve 42 is fixedly secured to an external wall 44 of the ventilator 26 as by screws 46. Mounted internally of the support 24 is an air spring assembly 48. Air spring assembly 40 includes an elongated air tight plenum 60 fixedly secured by bolts 61 to the base 20 of cart 18. A coil spring 62 resides in the bottom of the plenum 60 and provides assistance in lifting the weight of the ventilator 26 when adjusting the ventilator from the low position to the high position. The coil spring 62 acts upon a block or piston 64 which is fixedly secured to the lower end of a hollow cylinder or piston rod 66. The upper end of cylinder 66 is connected to the sleeve 42 via a bracket 68. Contained within the cylinder 66 is a rod 70 which extends downwardly through an aperture 72 in the block 64 and has on its lower end a valve 74 which seats against the lower side of the block 64. The upper end of rod 70 is adapted to be moved vertically by a pivotable lever 76 which itself is an extension of a handle 78 mounted to sleeve 42 via a bracket 80. To facilitate this vertical movement of sleeve 42 and hence lever 76, the uprights 24 have a vertical slot 79 through which the bracket 68 extends. Block 64 includes around its periphery a suitable seal 90 to prevent air from transferring between the two cavities of plenum 60 defined by the block 64. A seal 92 is utilized at the upper end of plenum 60 to allow the cylinder 66 to travel vertically with respect to the plenum 60 without loss of air therefrom.

It will be appreciated that upward motion of handle 78 causes downward motion of lever 76, the end of which contacts the upper end of rod 70. Continued upward motion of handle 78 causes the lever 76 to force rod 70 downwardly causing valve 74 to unseat from the lower surface of block 64. Rod 70 is spring loaded with respect to cylinder 66 internally by means not shown, such that when handle 78 is released, lever 76 rises thereby releasing rod 70, which then returns to its normal state with valve 74 seated against the lower surface of block 64. The handle 78 may, if desired, also be spring biased to a released position shown but it is anticipated that the weight of handle 78 will overcome the weight of lever 76 and release itself by gravity.

When handle 78 is raised upwardly thereby depressing the upper end of rod 70 downwardly by virtue of the lever 76, it will be appreciated that air may freely travel through ports 71 in cylinder 66 and aperture 72 in block 64 to equalize the volume of air on both the upper and lower sides of the block 64. As handle 78 is additionally raised upwardly, sleeve 42 slides upwardly on post 24 and cylinder 70 and block 64 slide upwardly within plenum 60. Air volume is thereby equalized on either side of the block 64. When the ventilator 26 has been moved into its desired upward position, handle 78 is released, thereby causing valve 74 to reseat, the volume of air trapped therebelow by virtue of block 64 and seal 90 preventing the weight of the ventilator 26 from moving it downwardly. Of course, the force of coil spring 62 aids in overcoming the weight of the ventilator 26 when raising same, and must be overcome by downward force on the ventilator 26 when moving same downwardly.

Many other devices and mechanisms could similarly be employed to raise and lower the ventilator 26 on supports 24, and the invention is not limited to the specific embodiment illustrated, as same is only for illustrative purposes. Furthermore, such a device or mechanism could as easily be foot operated rather than hand operated.

Referring back now to FIGS. 1 and 2, the critical care bed assembly 10 includes a patient support surface or bed 100 with appropriate side guards 102, mounted onto a bed base 104 with suitable supporting structure 106, shown schematically. Bed base 104 includes a generally Y-shaped base frame 110 which includes outspread arms 112, 112 and a stem 113, and wheels or casters 114 mounted to the ends of the outspread arms 112, 112 and to a crosspiece 113a at the end of the stem 113. The outspread arms 112, 112 are adapted to receive the mobile ventilator assembly 12 therein, when the ventilator assembly is in its lowered compact configuration, as is illustrated in FIG. 1.

A suitable mechanical latch 116 is located generally within the trough area of the outspread arms 112, 112 and is employed for removably securing the mobile ventilator assembly 12 to the bed base 104. A suitable cooperating latch mechanism 118 is located on the rear side of the ventilator 26 in a suitable location to mate with bed latch 116 when the ventilator assembly 12 is at the lowered position of FIG. 2. While the cooperating latch 118 is illustrated as being mounted to a cross piece (not shown) of the ventilator 26, it could just as easily be mounted to a cross-piece (not shown) of the base 20 of the ventilator cart 18.

The bed 100 mounted to the bed base 104 generally includes suitable electrical controls for varying the height of the bed 100 above a floor surface by changing the attitude of the supporting structure 106. In order to prevent the bed 100 from being lowered onto the mobile ventilator assembly 12 when same is docked to the bed base 104, there is provided with the latch 116 a suitable switch 120 for disabling this high/low function of the bed 100. Most any suitable switch 120 could be utilized, and could be of, for example, the optical, mechanical or ribbon type.

To provide for uninterrupted operation of the ventilator 26, a suitable DC power supply 122 is provided. While the power supply 122 could be contained within the ventilator 26, mounted to the ventilator cart base 20, or could even be a part of the bed supporting structure 106, it is preferably mounted to the bed base 110. Suitable cables 124 connect the power supply 122 to the ventilator 26. Ideally, connecting cables 124 to the ventilator 26 would immediately internally to the ventilator 26 disconnect the AC power provided by the AC outlets 34 and immediately switch the ventilator over to DC power supplied by the power supply 122. Cables 32 could then be unplugged from their respective AC ventilator outlets 34 thereby providing for continuous operation of and elimination of any downtime associated with the ventilator 26 during transportation of the bed assembly 10 and ventilator assembly 12 to another location.

Referring to FIG. 2, it will be noted that the periphery of the bed 100 when projected downwardly onto the floor therebelow defines a footprint 126. As can be seen in the nested configuration, the mobile ventilator assembly 12 falls well within this footprint 126. Therefore, a hospital care provider normally adept at maneuvering the critical care bed assembly 10 need not have to account for a larger footprint in maneuvering the combination through doors, down aisles and into elevators. The care provider can simply maneuver the critical care bed assembly 10 as before, and without the necessity of individually rolling the mobile ventilator assembly 10 therebeside when transferring the equipment from one hospital room to another. Furthermore, the need to hurriedly transfer the equipment from one room to another and hence from one wall AC source to another wall AC source is eliminated.

Other variations of a combination hospital bed and ventilator are contemplated by the invention. For example, the ventilator could be separated from its wheeled cart and docked to the hospital bed base, to the supporting structure which mounts bed to base, or even the hospital bed itself underneath a head section thereof. All such variations would provide a hospital bed-ventilator combination, which combination is rollable as a single unit, with the ventilator being positioned within the footprint of the bed.

With reference to FIG. 4 there is illustrated a preferred embodiment of the ventilator cart of the present disclosure. The ventilator cart 150 includes an outermost rectangular base frame 151 which has sides 152, 153, 154 and 155. The cart 150 also includes an innermost rectangular support frame 156 which has sides 157, 158, 159 and 160. Innermost support frame 156 telescopes upwardly and downwardly with respect to the outermost base frame 151. The outermost frame 151 has fixedly secured thereto a pair of standards or uprights 161a and 161b, the lower ends of which are fixedly secured to frame sides 154 and 155, respectively. Fixedly secured to each standard 161a and 161b is a vertical slide 162, such as the type marketed under the trademark Accuride®.

Referring to FIG. 5, it can be seen that each vertical slide 162 includes a plate 163 which is fixedly secured to a mounting block 164 via fasteners 165. Plate 163 includes a pair of inwardly facing legs 163a. Block 164 is secured to the upper end of each of the standards 161a and 161b. Vertical slide 162 further includes a rail 166 which is mounted for vertical translational movement with respect to the plate 163 via a number of steel balls 167 held within a vertically slidable ball retainer 179. A strap 178 encircles the vertical extent of the ball retainer 179, has ends fixed to the rail 166 at a point approximately midway of the vertical extent of the rail 166, and is secured to the plate 163 at 163b. Balls 167 in retainer 179 ride between the outer sides of the legs 163a of plate 163 and inwardly turned portions 166a of rail 166. It will be appreciated that legs 163a, balls 167 and inwardly turned portions 166a effectively function as a linear ball bearing assembly. Rail 166 is itself secured to mounting bar 168 which is, in turn, secured to a ventilator (phantom lines) via appropriate hardware 169.

At the upper end of each mounting bar 168 there is an ear 170 which is attached to the upper end of an air or gas spring 171. The lower end of each mounting bar 168 is fixedly secured to the sides 159, 160, respectively, of the frame 156. At the lower ends of each air spring 171 there is provided a clevis 172 which is secured to the piston 173 of the air spring 171. The clevis 172 is pinned via a pin 174 to an ear 175 one of which is located at each forward corner 176, 177 of the outermost frame 151. Legs 180 are provided for securing casters 181 to the outermost frame 151.

A ventilator (phantom) to be secured to the ventilator cart 150 rests atop the innermost support frame 156 and is secured to the mounting bars 168 via the fasteners 169. The angled orientation of the gas springs 171 allows for proper vertical travel of a ventilator supported by the cart 150, while simultaneously allowing one to physically overcome the force of the gas springs in order to force the ventilator downwardly into a nested configuration without any undue difficulty.

In order to actuate the gas springs 171 to raise the ventilator from its lowered position to its raised position, there are provided a pair of levers 185 located beneath the forward side 152 of the outermost frame 151. Each lever 185 includes a dog leg portion 186 which can be actuated by a foot of a care provider. Dog leg section 186 is connected to a linear section 187 which terminates in a hooked portion 188. Hooked portion 188 is positioned directly underneath the actuating rod 190 of the gas spring 171. The levers 185 are supported within tabs secured to the side 152, such as that shown at 192. Downward movement of the dog leg section 186 of each lever 185 causes upward rotation of the hooked portion 188, which actuates the actuating rod 190 of the air spring thereby enabling a care provider to manually raise the ventilator aided of course by the upward thrust of the gas spring 171.

It will be appreciated that the ventilator cart described herein can be used in any number of applications where a particular piece of medical equipment is desired to be rollably transported and selectively raised and lowered. Therefore, the cart is not to be limited solely for use in conjunction with ventilators and is claimed to have application to any number of different types of medical equipment.

With reference to FIGS. 6-11, and with like numbers representing like components, there is illustrated a care cart 200 for use in conjunction with the critical care bed 10 and mobile ventilator 12. The care cart 200 has a pentagonal base 201 with three casters 202 secured thereto for rolling the care cart 200 from place to place. A blow molded housing 203 is mounted atop the base 201 and houses one or more batteries 204, a battery charger 205 and a compressor 206. A pair of posts 207, 207 extend upwardly from the rear of the base 201, and a single post 208 extends upwardly from the front of the base 201 approximately half the vertical distance of the rear pair of posts 207, 207. A platform 209 is connected between the pair of posts 207, 207 and the single post 208 and is adapted to support four E-size oxygen and/or air tanks 216. The platform 209 has a transverse front support 210, a transverse rear support 211, and a plurality of longitudinal support rods 212 spanning between the front and rear supports 210 and 211, respectively. The rear ends 214 of the outwardmost longitudinal support rods 212a are secured to the rear pair of posts 207, 207 at 207a. Forward transverse support 210 is secured to the forwardmost vertical support 208 at 208a. The rearwardmost transverse support 211 includes semicircular notches 211a which receive the neck portions 215 of oxygen and/or air bottles 216. A semi-circular transverse support structure 217 is secured to the underneath side of the platform 209 for supporting a custom air tank 218 therein.

A shelf 219 projects forwardly from the upper ends of the pair of posts 207, 207. The shelf 219 includes a rectangular cutout 220 along its rear edge which forms a gripping bar 221 which can readily be grasped by a care provider for pushing the cart 200 from place to place. Gussets 222 are mounted between the shelf 219 and the pair of posts 207, 207 to provide additional rigidity for the shelf 219.

A manifold 223 is mounted near the lower ends of the pair of posts 207, 207. The manifold includes a plurality of connections 224 for connecting the air and oxygen bottles 216 thereto, as with supply lines 225. In order to supply the ventilator 12 of the present disclosure with DC electricity, air and oxygen from the care cart 200, supply lines 226, 227 and 228, respectively are provided for connecting to an electricity/air/oxygen controller box 240, which itself is connected to the ventilator 12 (FIG. 8), the operation of which will be subsequently described.

Figure 7:
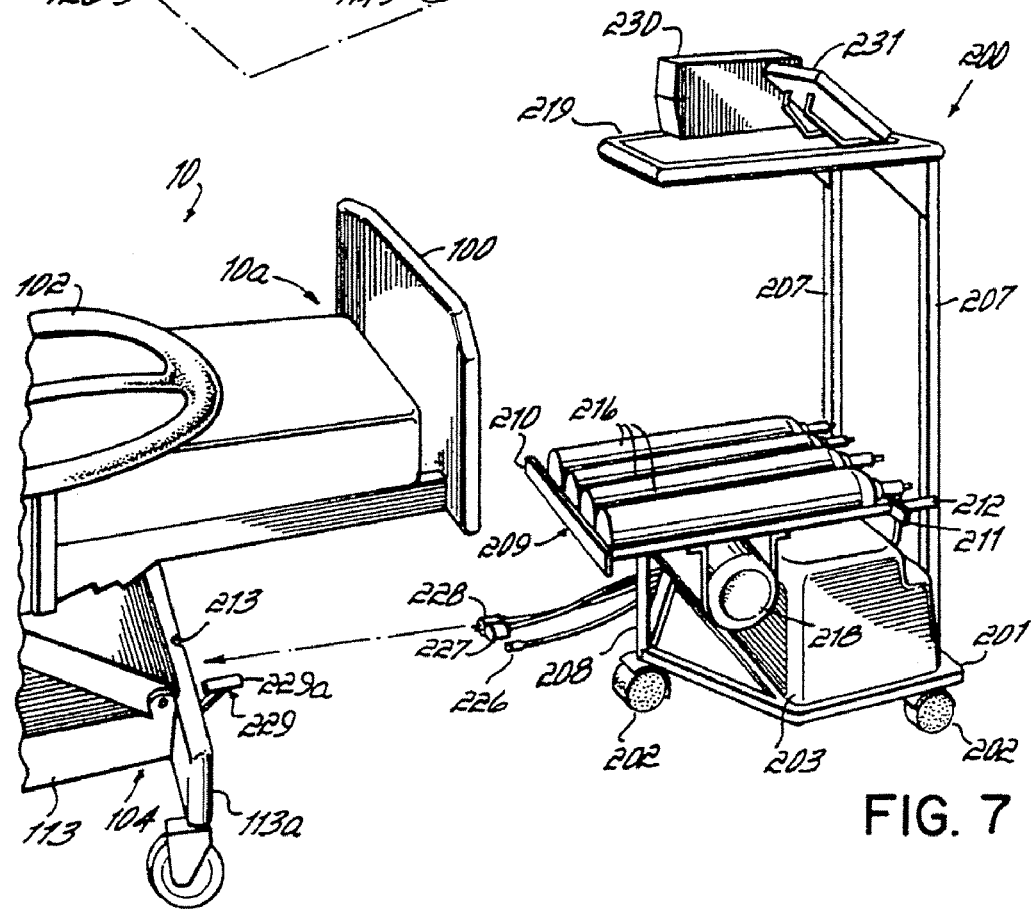
FIG. 7 is a perspective view of the care cart docking to a hospital bed.

With reference to FIG. 7, the care cart 200 is illustrated as approaching the critical care bed 10 for docking under a foot section thereof. On the crosspiece 113a of stem 113 there is pivoted a foot actuated lever 229 which is employed for latching the cart 200 to the bed 10. Upon docking the cart 200 with the bed 10 the forwardmost supporting post 208 enters into a concavedly cylindrical recess 213 in the crosspiece 113a. The lever 229 is then toggled upwardly as by a care provider's foot applying upward force to cross bar 229a, which upward toggling causes the lower end (not shown) of the lever 229 to pivot downwardly and rearwardly of the support post 208 thereby securing the support post 208 within the concavedly cylindrical recess 213 in the crosspiece 113a.

Numerous ancillary items can be employed with the care cart 200. For example, a drug box 230 can be incorporated on or into the shelf 219. A display monitor 231 can likewise be supported on the shelf 219 for displaying patient care data during transport of the patient on the bed 10 from one location to another.

Figure 8:
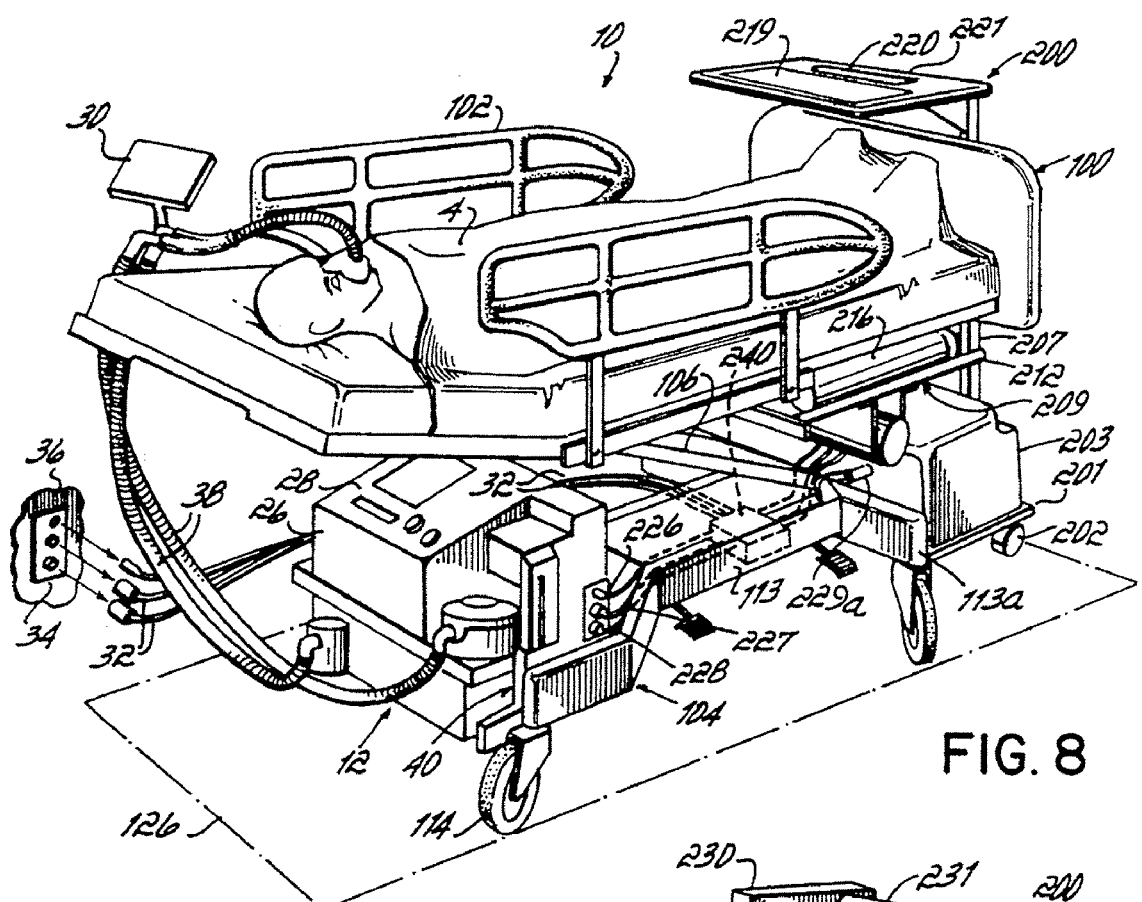
FIG. 8 is a perspective view of the care cart docked to a hospital bed.

With reference to FIG. 8, the care cart 200 is illustrated as being fully docked to the critical care bed 10, supplying ventilator 12 with DC electricity, oxygen and air during transport of the bed 10, ventilator 12 and cart 200. It will be seen that the ventilator 12 and cart 200 nestably fit within the mobile footprint 126 of the hospital bed 10. More particularly, and with respect to the care cart, it will be seen that platform 209 and shelf 219 are spaced apart vertically by a sufficient distance such that clearance is provided for footboard 100 on the bed 10. Therefore, when docked to the bed 10 (FIG. 8), platform 209 underlies the foot end 10a of the bed while shelf 219 overlies the foot end 10a of the bed 10. Further, it will be seen that stem 113 along with crosspiece 113a on bed base 104 are spaced a sufficient distance inwardly from the foot end 10a of the bed 10 to allow the base 201 and supporting platform 209 of cart 200 to completely come within footprint 126 of bed 10 (FIG. 8).

Figure 9:
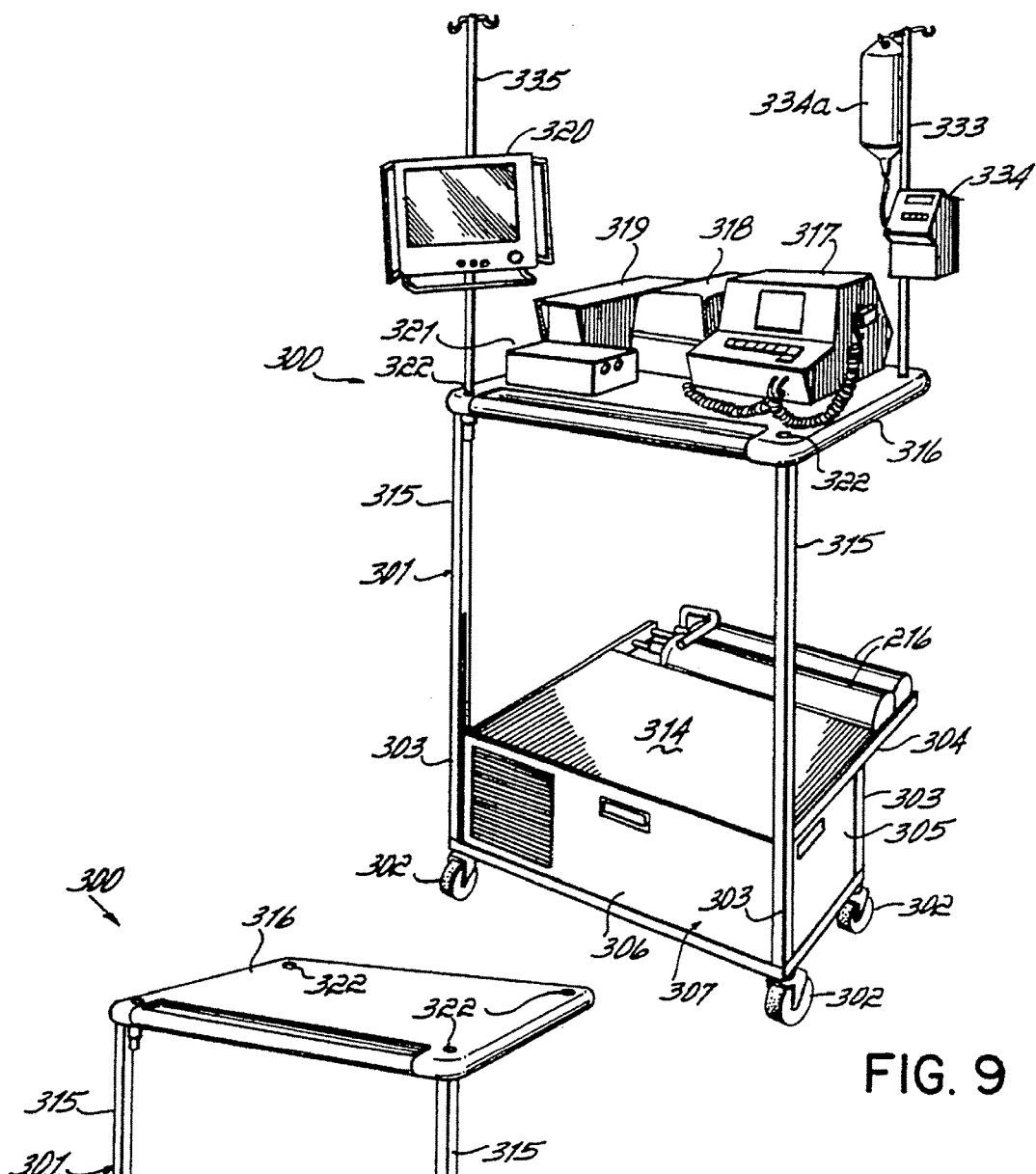
FIG. 9 is a perspective view of another embodiment of the care cart of the present disclosure.
Figure 10:
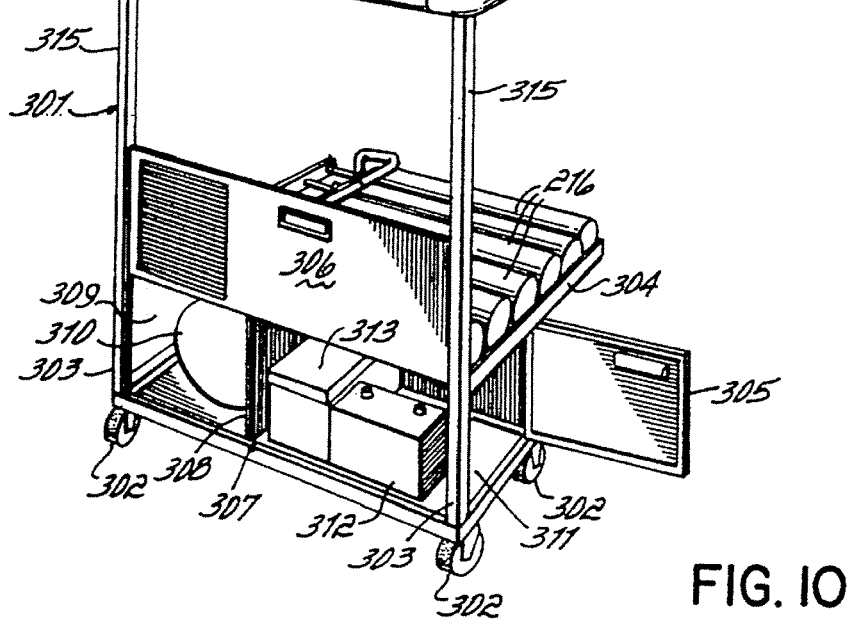
FIG. 10 is a perspective view of the care cart of FIG. 9 with doors opened and access cover removed.

Referring to FIGS. 9 and 10, there is illustrated another embodiment of the care cart designated by the numeral 300. The cart comprises generally a base 301 including casters 302, four housing corner supports 303 and a horizontal support frame 304 secured to the upper ends of corner supports 303. Base 301 and support frame 304 define a space which is enclosed with a pair of pivoting end doors 305, 305, an upwardly slidable, removable rear panel 306 and a forward panel (not shown). Side doors 305, rear panel 306 and the front panel are preferably of sheet metal fabrication. Side doors 305, rear panel 306, front panel, base 303 and supporting frame 304 define generally a housing 307 which includes an interior wall or divider 308 (FIG. 10) also of sheet metal construction. Divider 308 defines one compartment 309 which houses a liquid oxygen system 310 and another compartment 31 which houses batteries 312 and a battery recharger 313.

Supporting frame 304 includes provision for supporting six E-size oxygen and/or air tanks 126 thereatop (FIG. 10), or alternatively a removable shelf 314 (FIG. 9) can be snapped atop the frame 304 to provide additional shelf space in which case two E-size tanks 126 (FIG. 9) may still be supported atop the remaining portion of the supporting frame 304 which projects forwardly from underneath the shelf 314. A pair of uprights 315, 315 extend upwardly from the rear corner posts 303 of the housing and terminate in a forwardly projecting shelf 316, as in the prior embodiment.

Supported atop the supporting shelf 316 are a number of items employed in a critical care scenario, including a defibrillator 317, a drug box 318, a portable suction unit 319, and a transport monitor 320. Transport monitor 320 is powered by a tram 321 which, being a modular unit itself, is pluggable into a fixed monitor (not shown) in a typical critical care hospital room as part of, for example, a headwall unit or power column. The corners of the shelf 316 include I.V. pole sockets 322 therein such that I.V. poles 333 may be slipped therein, which support I.V. pumps 334 and I.V. solution bags 334a. Previously mentioned transport monitor 320 is likewise supported on a pole 335 which fits into one of the sockets 322 in the shelf 316.

In use, the care cart 200 or 300 of the present disclosure (the embodiment of either FIGS. 6-8 or FIGS. 9 and 10), is docked to the foot end 10a of a critical care hospital bed 10 and secured thereto with the foot actuated lever 229. The DC electricity, air and oxygen lines 226, 227 and 228 from the care cart are then connected to the electricity/air/oxygen controller box 240 which is itself connected to the ventilator 12 which is docked to the head end of the bed 10. This electricity/air/oxygen controller box 240 controls the flow of air, oxygen, DC power and AC power to the ventilator 12 from the head wall at the head of the bed 10 and the care cart 200 or 300 at the foot of the bed 10 during various stages of transport of the bed 10, ventilator 12 and cart 200 or 300. The controller box 240 is located on the bed base frame 110 adjacent the ventilator 12, and has three operating conditions or scenarios.

In the first condition, with the controller box being connected to oxygen and air at the wall, both oxygen and air are supplied to the controller box from the wall at 50 psi. With no care cart docked to the foot end of the bed, there is obviously 0 psi of oxygen and air supplied to the controller box from the foot of the bed. The controller box routes 50 psi oxygen and air to the ventilator.

In the second condition, again with the controller box connected to oxygen and air at the wall, wall oxygen and air are again supplied to the controller box at 50 psi. The care cart is now docked to the foot of the bed, supplying the controller box with 40 psi oxygen and air. With the bed in a stationary, semi-permanent position at the wall in the hospital room, the controller box closes the 40 psi oxygen and air supply from the cart at the foot of the bed and again routes 50 psi oxygen and air from the wall to the ventilator.

In the third condition, with the bed severed from its 50 psi wall oxygen and air during transport, the supply from the head end of the bed is 0 psi. With the care cart docked to the foot end of the bed during transport, and supplying 40 psi oxygen and air to the controller box, the box routes the 40 psi oxygen and air supply from the cart at the foot end of the bed to the ventilator, thereby supplying the ventilator with oxygen and air during transport.

The controller box further includes provision for routing AC and DC from the wall and care cart to the ventilator. When the bed is connected to AC at the wall, the box routes the AC to the ventilator which converts the AC to DC internally. When the bed is disconnected from AC at the wall, the box routes DC from the care cart to the ventilator.

After severing the bed from its AC electricity, oxygen and air supply at the wall, then, the bed, ventilator and care cart may thereafter be rolled about from place to place as a single unit by a care provider, normally by grasping the handhold built into the rear edge of the shelf of the care cart, the care cart providing total mobile support for the ventilator and bed, and hence patient 4.

Figure 11:
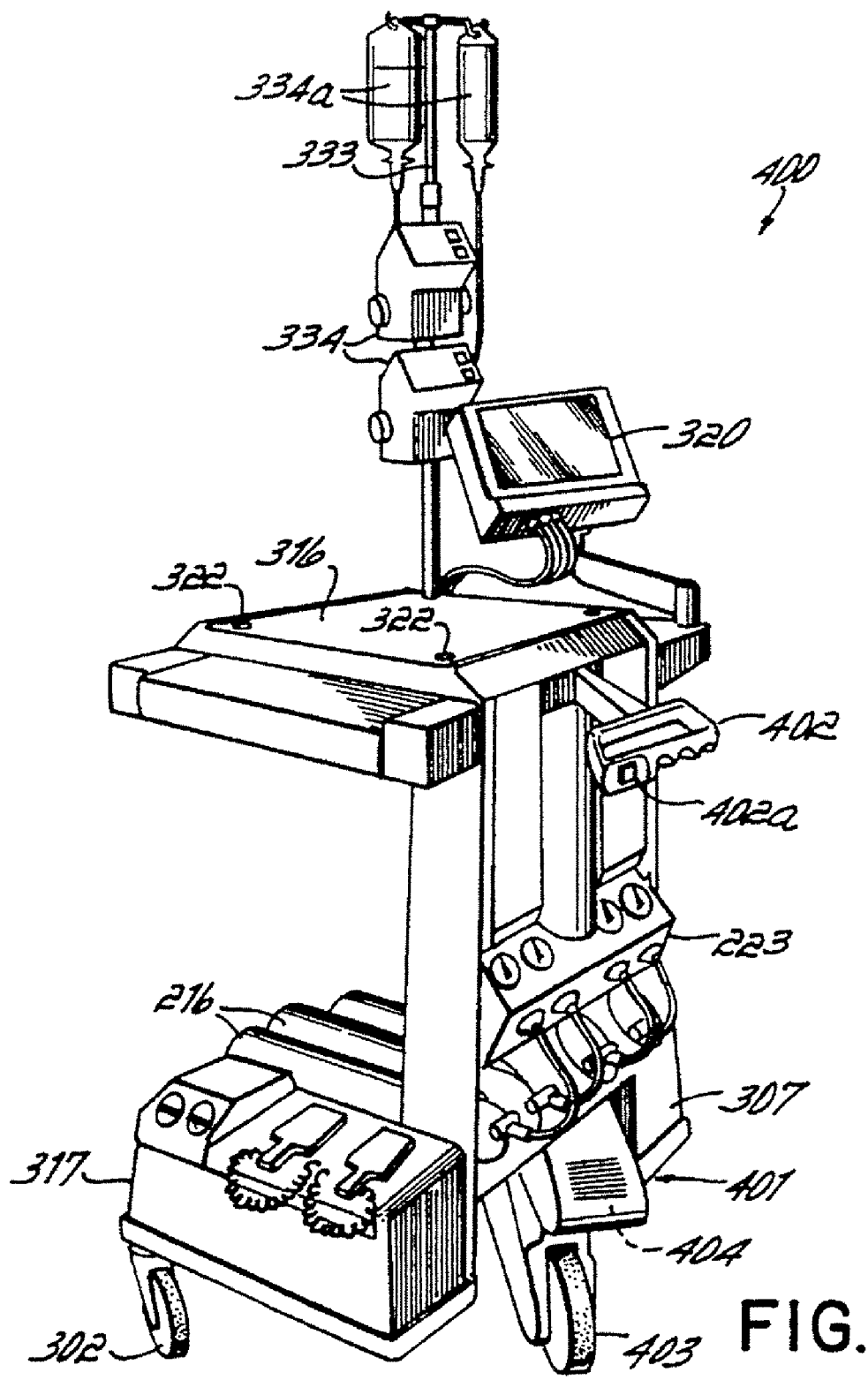
FIG. 11 is a perspective view of yet another embodiment of the care cart incorporating a motorized pilot jack therewith.

With reference to FIG. 11, and with like numbers representing like components, there is illustrated yet another embodiment of the care cart of the present disclosure designated generally by the numeral 400. In this embodiment, the cart includes all of the features of the former embodiments, with the additional feature of a motorized dolly or pilot jack 401 being included integrally with the care cart for motorized transport of the bed, ventilator and care cart. The pilot jack 401 includes a handle 402 which can be pivoted transversely with respect to the cart 400 for steering a drive wheel 403, which drive wheel is powered by a suitable motor 404. Pressing button 402a on handle 402 activates motor 404 driving wheel 403 in a forward direction. The motorized care cart 400 aids in overcoming the substantial increase in inertia generated by docking ventilator 12 and cart 400 to the bed 100. A suitable braking mechanism (not shown) would be incorporated within the cart 400 to aid in bringing the assembly to a stop. Preferably this pilot jack equipped care cart will be able to move 1500 lbs. of load and reach velocities up to 6 ft/sec. Preferably the pilot jack equipped care cart will have infinite variability in velocity control, including in both the forward and reverse directions. Preferably electrolyte deep discharge lead acid batteries will be used to power the pilot jack via a permanent magnet DC motor.

Other variations of the care cart are contemplated by the present invention. For example, other items can be incorporated into the cart in addition to those illustrated in the Figures, and in particular in FIG. 9. For example, a two-way communications system could be incorporated within the care cart for communications between the care provider transporting the patient atop the bed 10 and, for example, a care provider at the patient destination. Further, a lighting system could be incorporated into the care cart of the present disclosure to provide illumination for the care provider either for tasks to be performed on a patient or, for example, to light a hallway during transport of the patient atop the bed 10 during, for example, power outage. Furthermore, the care cart of the present disclosure could be adapted to support a miniaturized ventilator, known as a "transport vent".

The devices of the present disclosure have numerous advantages. A reduction in labor involved in preparing and transporting a critical care patient is effected. The total number of personnel required to transport a patient is reduced as well. The weight of the bed and the other devices utilized in conjunction with the bed is reduced which minimizes the physical effort expended by care providing personnel. The patient outcome is improved by giving the same care to the patient whether the patient is in the hospital room or in the hallway in transit between hospital rooms. And, all of the devices fit within the footprint of the bed to allow easy passage through doorways, around corners, and into elevators.

Figure 12:
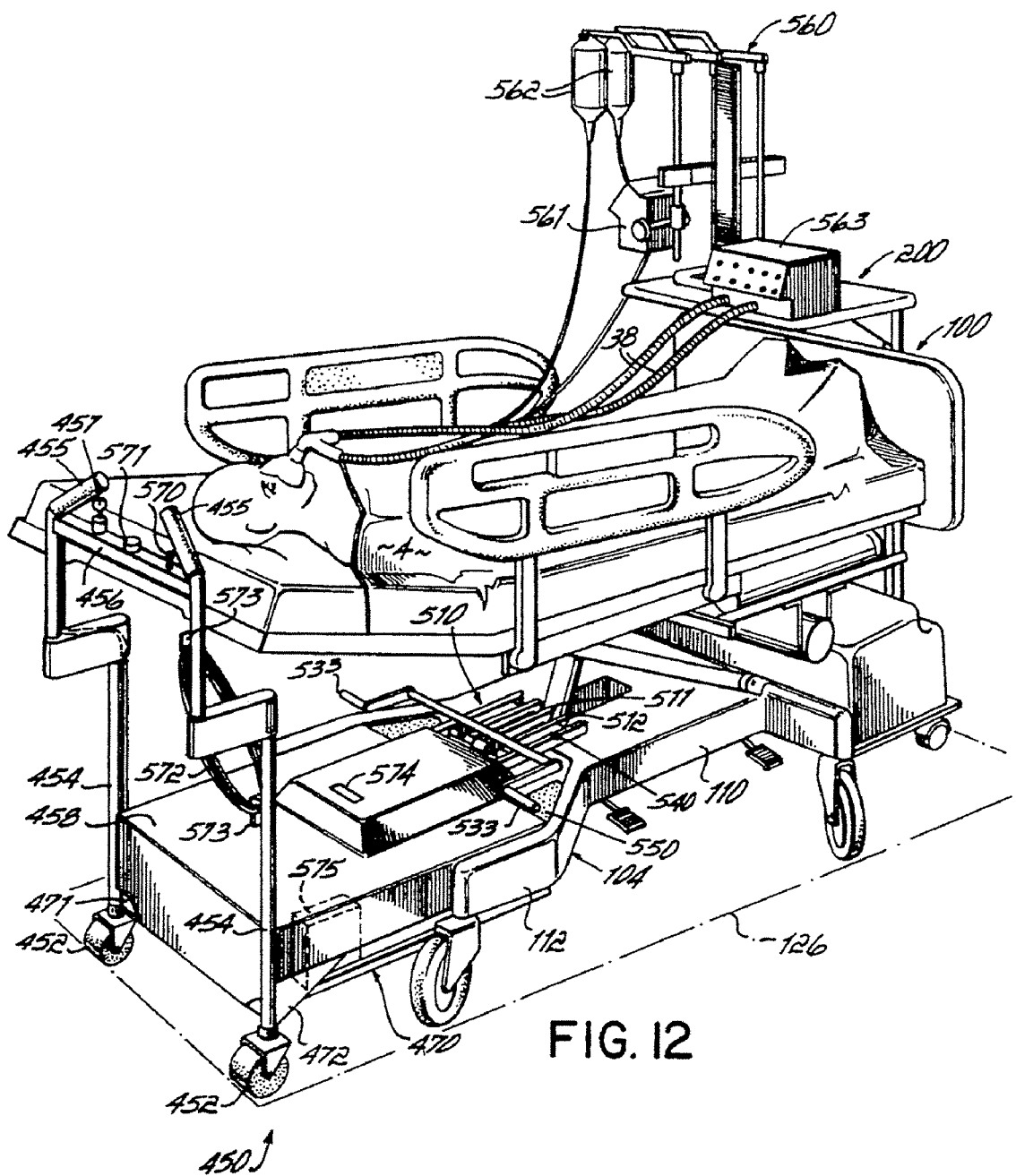
FIG. 12 is a perspective view of the motorized transport of the present disclosure docked to the head end of the hospital bed and with the care cart docked to the foot end of the hospital bed.

With reference to FIG. 12, and with like numbers representing like components, there is illustrated a motorized transport device or "mule" 450 for motorized transport of the bed 100 with care cart 200 docked thereto. Mule 450 docks to the generally Y-shaped base frame 110 of the bed base 104 within and between the outspread arms 112, 112, the frame for which can be fabricated of welded steel tubing or by casting of an aluminum bronze alloy which is weldable to steel. When the bed 100 is used in conjunction with the mule 450, the mobile ventilator assembly 12 is replaced with a miniaturized transport vent 563 which is supported atop the care cart 200, for supplying patient 4 with oxygen and air during transport. Additionally, care cart 200 can be adapted to support an IV rack 560 which includes mounted thereto an IV pump 561 for pumping IV solution from IV bags 562. As used herein, "bed" and "hospital bed" are deemed to generically embrace all rollable patient supports, such as stretchers, birthing beds, critical care beds, etc.

More particularly, and referring to FIGS. 12-20, the mule 450 has a base 451 with a pair of casters 452, 452 mounted on its rear corners. At the front of the base 451 and centered transversely of the base, there is a non-marking rubber drive wheel 453. Drive wheel 453 is located at approximately the center-of-mass of the bed 100 and care cart 200 combination. By so locating drive wheel 453, the bed 100 and care cart 200 may readily be pivoted about the center-of-mass of the combination when maneuvering the combination, thus facilitating transport of the combination. Extending upwardly from the rear of the base 451 are a pair of handles 454, 454, the upper ends of each of which are outfitted with a hand grip 455 for gripping the handles 454, 454. Mounted on a transverse support 456 spanning between the handles 454, 454, is a joy stick 457 of the wiperless type for use in controlling the drive wheel 453. A cover 458 (FIG. 12) is removably secured atop the base 451, covering the components mounted thereon.

Figure 13:
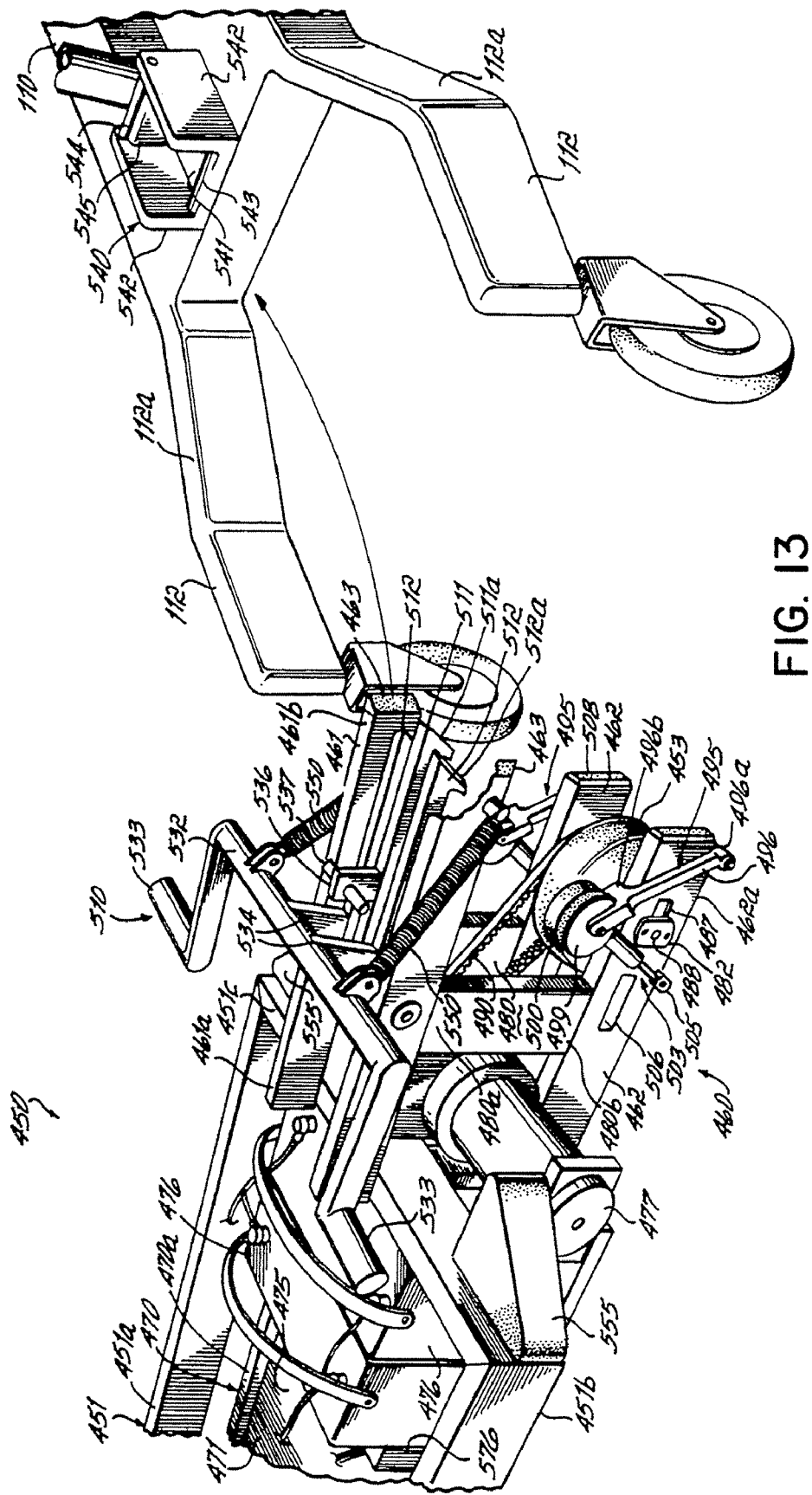
FIG. 13 is an enlarged, partial perspective view of the motorized transport approaching the y-shaped hospital bed base for docking thereto.
Figure 14:
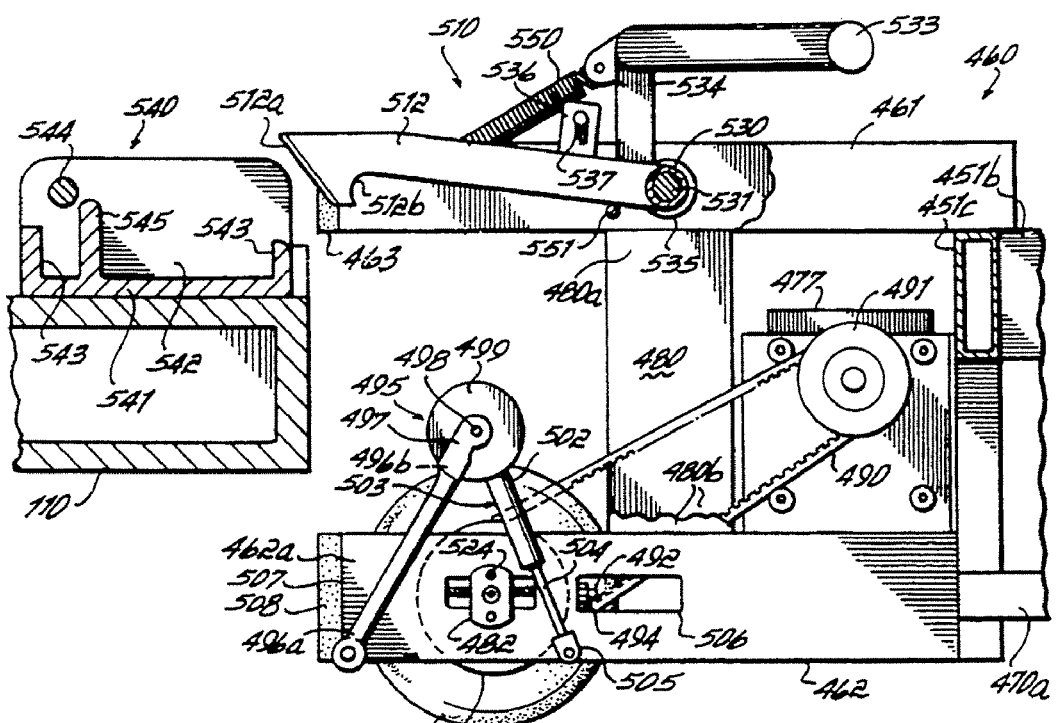
FIG. 14 is a partial side elevational view, in partial cross-section, of the motorized transport approaching the hospital bed base for docking thereto.
Figure 18:
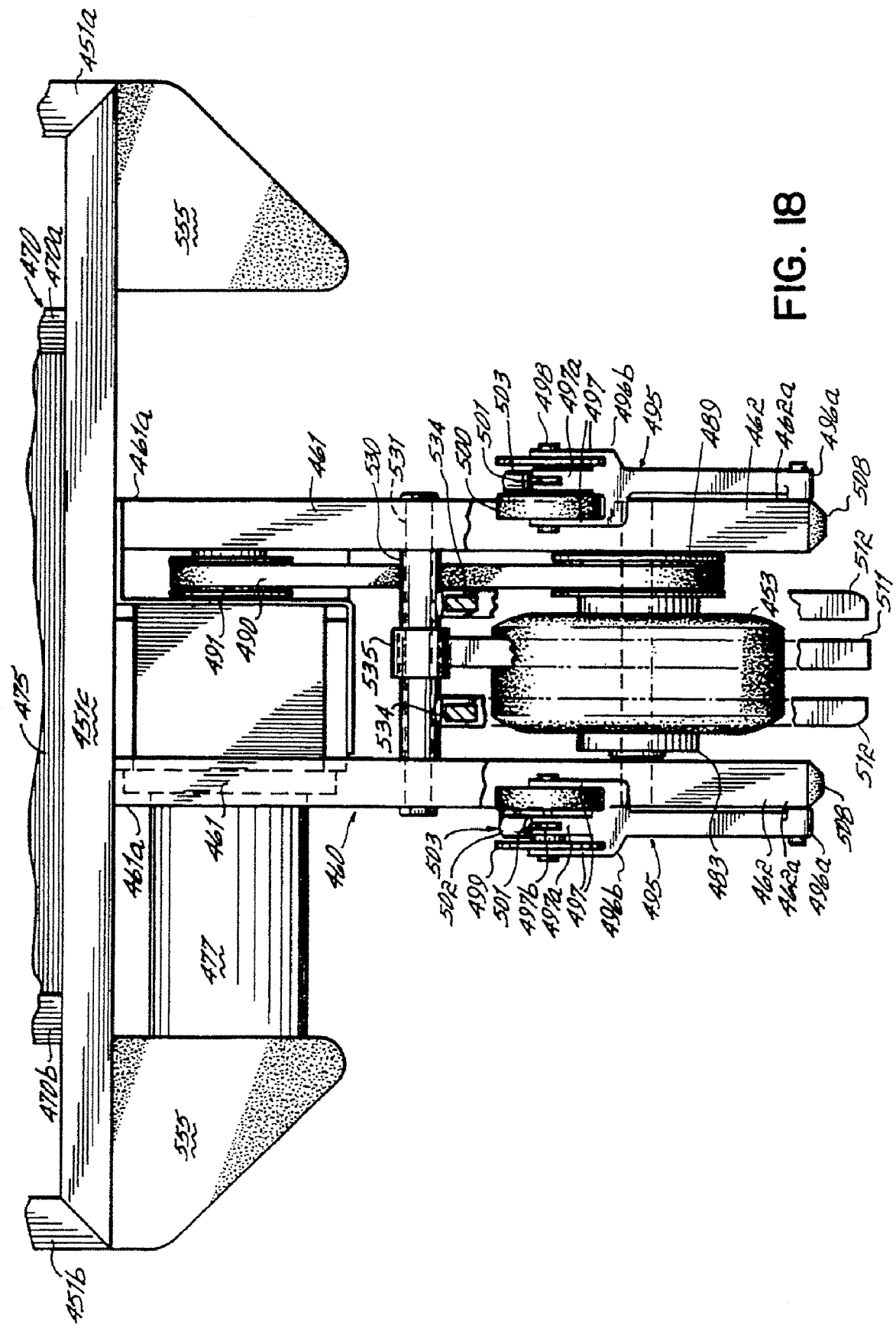
FIG. 18 is a top plan view of the front end of the motorized transport.
Figure 19:
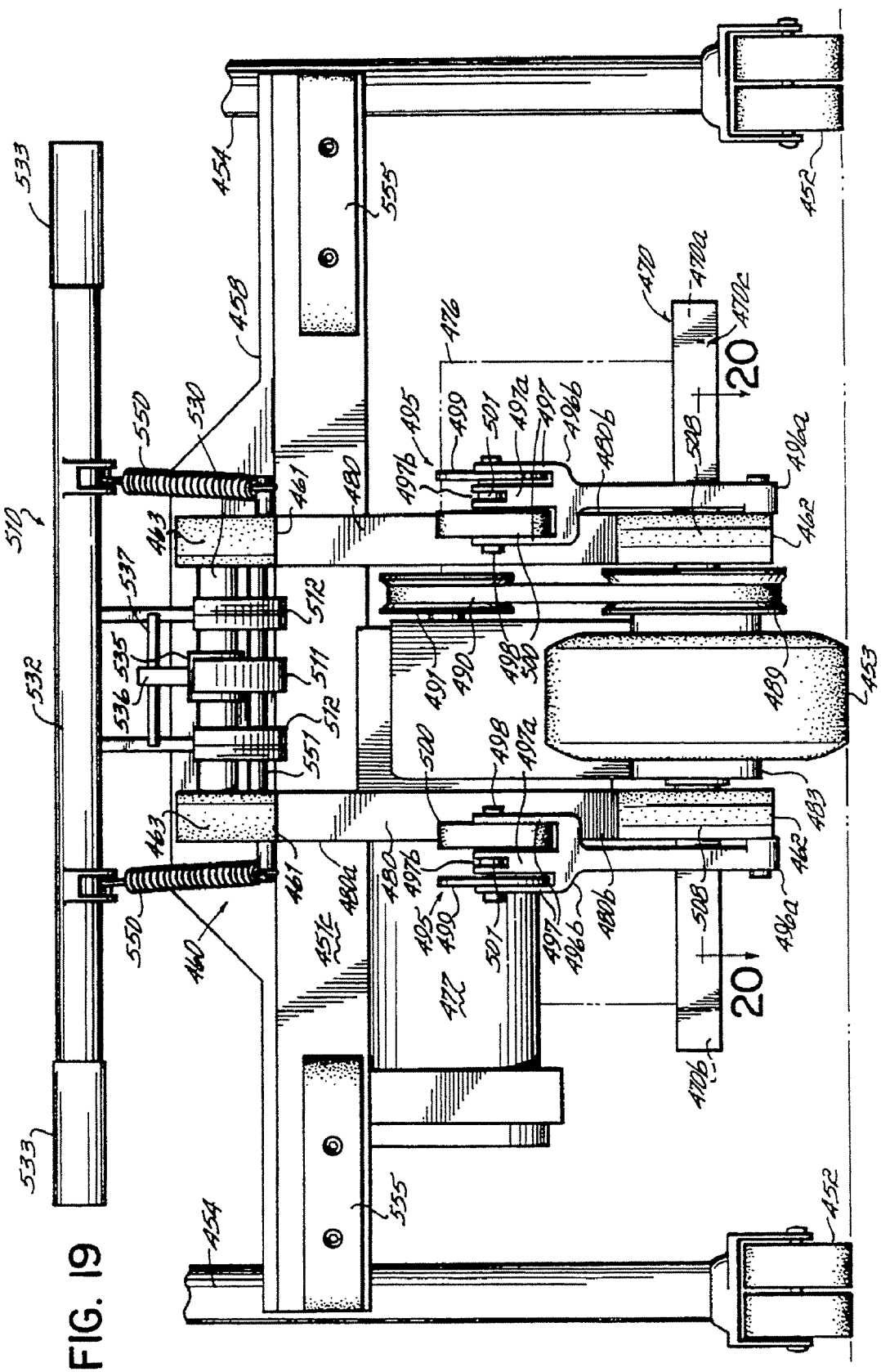
FIG. 19 is a partial front elevational view of the motorized transport.

Referring to FIGS. 13, 18 and 19, base 451 includes longitudinally oriented beams 451a and 451b which are fixedly secured together at their forwardmost ends by a transversely oriented beam 451c. Fixedly secured to the forward transverse beam 451c of base 451 is a drive wheel support structure designated generally by the numeral 460. Drive wheel support structure 460 includes an upper fork comprising a pair of supports 461, 461 and lower fork comprising a pair of supports 462, 462. The upper pair of supports 461, 461 have rear ends 461a, 461a which are fixedly secured to the upper edge of transverse support 451c of base 451. The forward ends 461b, 461b of support pair 461, 461 each include a nylon wedge 463 secured thereto, the necessity for which will be subsequently described.

Spaced underneath the supports 451a, 451b and 451c is a rectangular frame 470 having sides 470a and 470b which are fixedly secured at their forwardmost ends to forward transverse frame member 470c. The aft ends of the frame members 470a, 470b are fixedly secured to a rear transverse plate 471 (FIG. 12) which forms the rear edge of the base 451, the transverse edges of which are fixedly secured to the handles 454, 454. Gussets 472, 472 (FIG. 12) tie the rear ends of members 451a, 451b into the lower ends of the handles 454, 454 above the casters 452, 452. Fixedly secured to the underneath side of the frame 470 is a pan 475. Supported atop pan 475 and within base 451 are a pair of batteries 476, 476 which are employed to power a motor/gear box 477. The batteries 476, 476 are preferably of the sealed, deep cycling type, and the motor/gear box 477 is preferably of the permanent magnet motor, helical gear box type.

Drive wheel support structure 460 further includes a pair of vertical supports 480, 480 each of which has upper and lower ends 480a, 480b fixedly secured to a respective one of the upper and lower horizontal support pairs 461, 461 and 462, 462.

Referring to FIGS. 13 and 18-20, drive wheel 453 is rotatably supported on a shaft 485 the ends of which are supported in blocks 486, 486. The ends of shaft 485 pass through slots 487, 487 in the forward ends 462a, 462a of lower support pair 462, 462. A screw 488 secures an end cap 482 onto each end of shaft 485. A driven gear pulley 489 is 15 fixedly secured to a cast iron drive wheel hub 483 with screws 484 and is driven by a Poly Chain® belt 490, which passes over drive pulley 491 which is fixedly connected to the output shaft of the motor/gear box 477. It will of course be appreciated that slots 487 in the supports 462, 462 allow fore and aft adjustment of drive wheel 453 in order to adjust tension in belt 490. Four allen head adjustment screws 492 adjust fore and aft travel of drive wheel 453, the bulkhead 493 in each of the support pairs 462, 462 being mateably threaded to accept a screw 492. Lock nuts 494 lock screws 492 against the bulkheads 493. The rearmost screws 492 and corresponding locknuts 494 are accessed through a slot 506 in each of the supports 462, 462, whereas the forwardmost screws 492 and corresponding locknuts 494 are accessed through an open forward end 507 in each of the supports 462, 462 by removing its respective nylon wedge 508.

On either side of drive wheel 453 there is a thrust washer 520, a needle type thrust bearing 521, another thrust washer 522 and a radial roller bearing 523. In order to load these components in compression to take the linear play out of these components along shaft 485, the end caps 482 are tightened onto the ends of the shaft 485. With blocks 486, 486 and hub 483 being slightly longer than the shaft 485, and as the caps 482 are tightened with screws 488, shaft 485 is placed in tension and the components on shaft 485 are placed in compression, thus removing any axial slop from the components on shaft 485. For adjusting shaft 485 between supports 462, 462, a pair of allen head screws 524 pass through one of the end caps 482 and bottom out against the side of the corresponding lower support 462. Advancing screws 524 inwardly removes any axial play of the shaft 585 from between the supports 462, 462.

Referring to FIGS. 13-19, on the outer side of each of the lower supports 462 there is a downward force generating mechanism 495 which, when the mule 450 is docked to the bed 100 generates a downward force on the drive wheel 453 to prevent the drive wheel 453 from slipping on a floor surface upon being rotationally accelerated by the motor/gear box 477. Each mechanism 495 includes an aluminum fork 496 which has a lower end 496a pivotally connected to the support 462. The upper end 496b includes a pair of spaced outside arms 497, 497, and a centermost arm 497a. A shaft 498 is fixedly secured to these arms 497, 497 and has rotatably supported thereon two wheels 499 and 500. Wheel 499 is essentially a relatively thin aluminum disk, whereas wheel 500 is a thicker nylon or glass filled nylon wheel. Pivotally supported to the shaft 498 between the wheels 499 and 500 and within slot 497b of center arm 497a is the upper end 501 of the cylinder portion 502 of a gas spring 503. Each gas spring 503 is preferably sized at 200 Newtons. The piston portion 504 of the gas spring 503 has its lower end 505 pivotally supported to the support 462. The distance between facing surfaces of the wheels 499 and 500 is sufficient to allow the upper end 501 of the cylinder portion 502 of the gas spring 503 to reside therein without coming into contact with or otherwise binding up against the inside surfaces of the wheels 499, 500 when the gas spring 503 is depressed.

Each of the mechanisms 495 generate downward force on the drive wheel 453 when the mule 450 is docked to the bed 100, as the wheels 499 and 500 of each of the mechanisms 495 roll underneath the bed base frame 110, the operation of which will be subsequently described in more detail.

Referring to FIGS. 13-19, a latching mechanism 510 is mounted on the drive wheel support structure 460 and is operable to latch the mule 450 to the bed base 110. The latch mechanism 510 includes three latch fingers: a centermost latch finger 511 and a pair of outer latch fingers 512, 512. Each of the three fingers 511 and 512, 512 includes upwardly ramped forwardly presenting surfaces 511a and 512a, 512a respectively, and radiused hook portions 511b and 512b, 512b respectively. The outer latch fingers 512, 512 are fixedly secured to a rotating sleeve 530 which rotates about a fixed shaft 531. A horizontally disposed bar 532 has rearwardly projecting handles 533. The bar 532 is rigidly connected to the rotating sleeve 530 by vertical links 534. The centermost latch finger 511 is itself rotatably connected to the rotating sleeve 530 with its own rotating sleeve 535. The centermost latch finger includes an upstanding tab 536 with a cross pin 537 press fitted therethrough.

Figure 15:
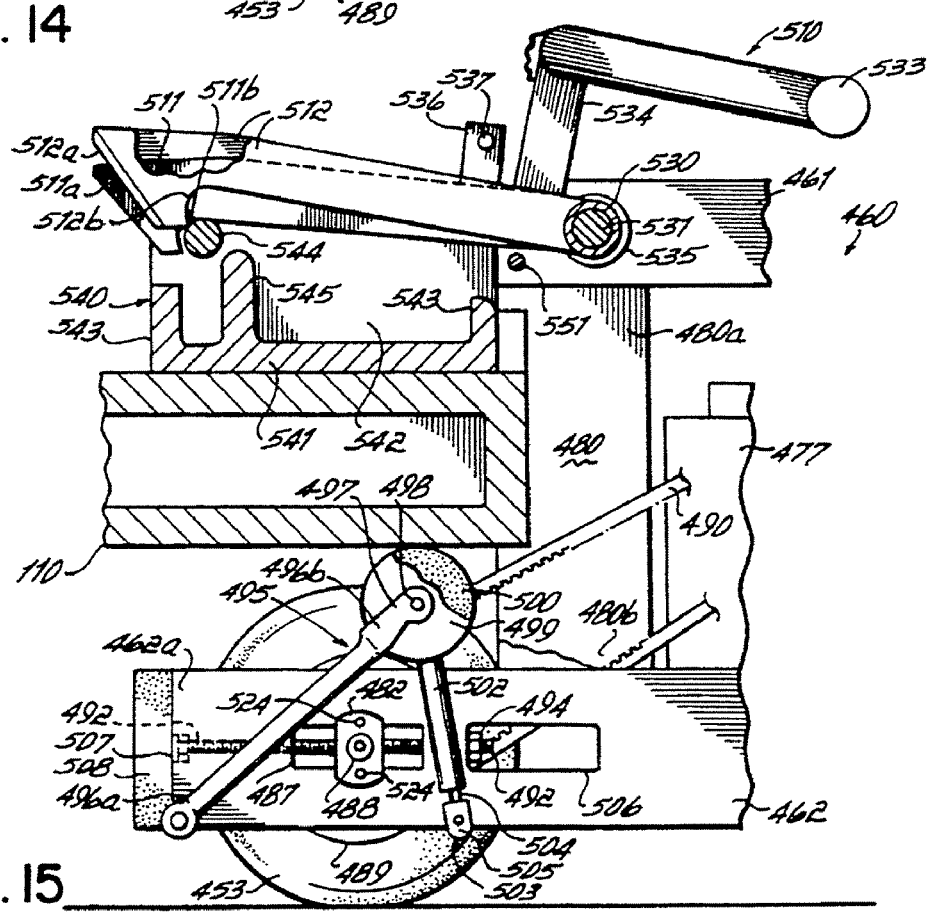
FIG. 15 is a partial side elevational view, in partial cross-section, of the motorized transport in the initial stage of docking to the hospital bed base.
Figure 16:
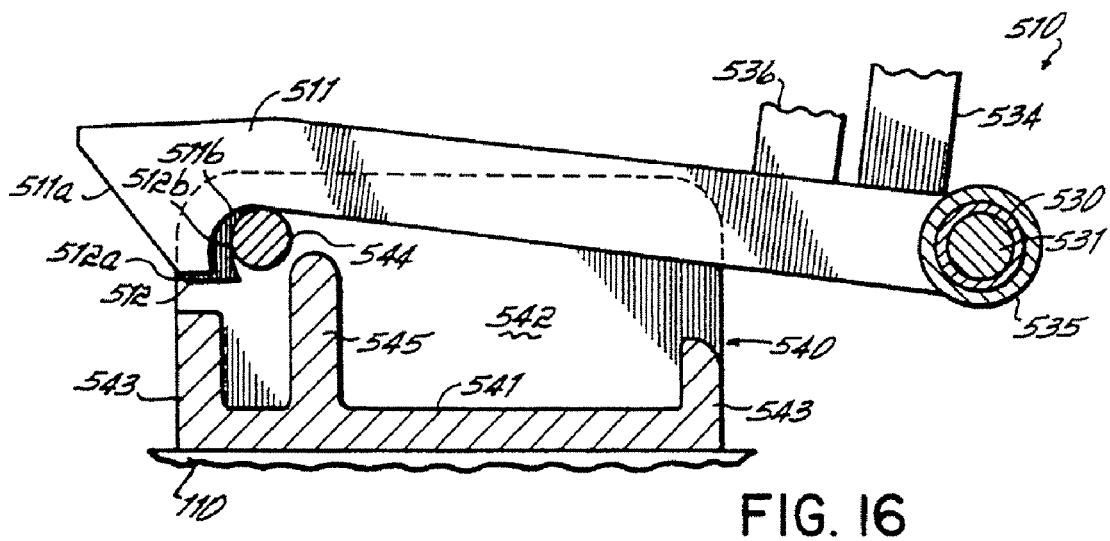
FIG. 16 is a partial side elevational view, in partial cross-section, of the latching fingers of the motorized transport latched to the hospital bed mounting block in the final stage of docking to the bed base.
Figure 17:
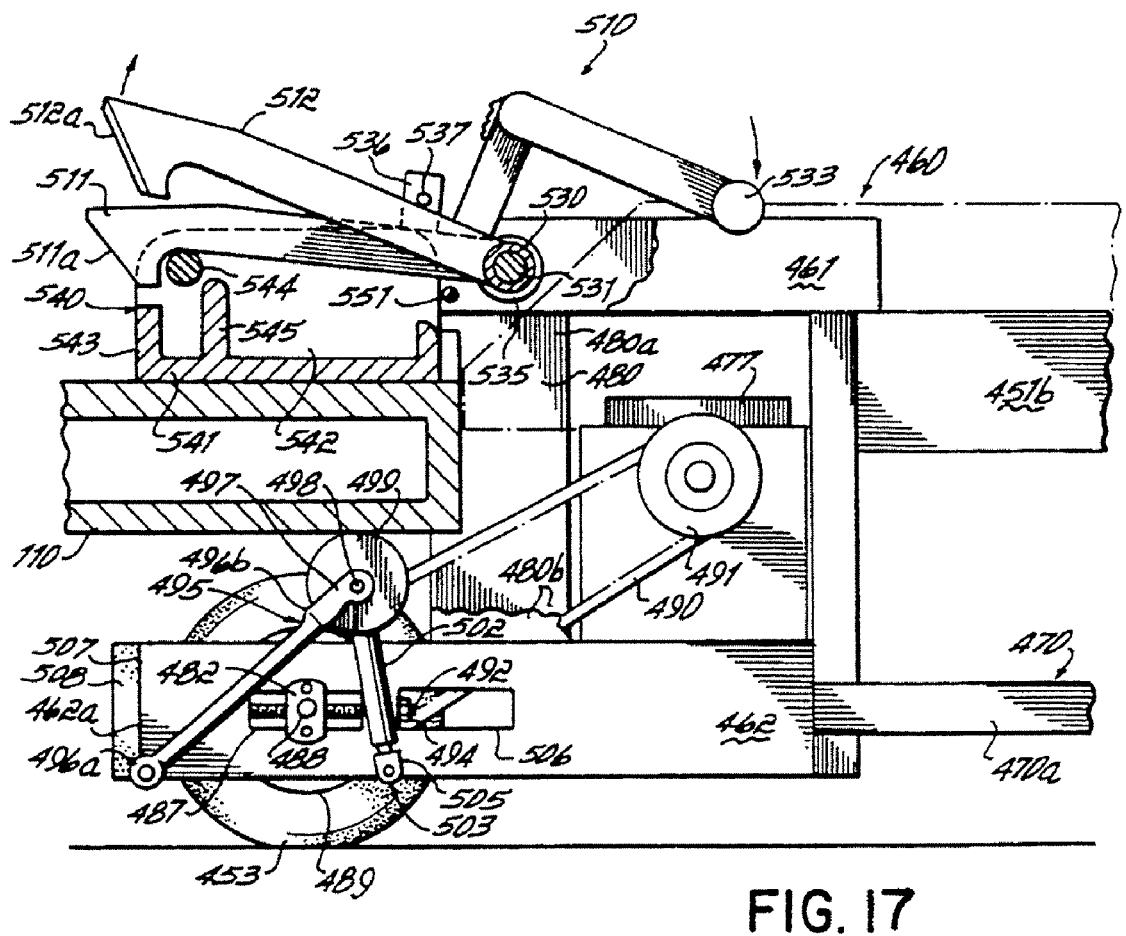
FIG. 17 is a partial side elevational view, in partial cross-section, of the motorized transport being released from the hospital bed base.

Referring to FIGS. 14-17, there will be seen a mounting block 540 for connection of the latching mechanism 510 thereto. The mounting block 540 is attached to the upper side of the bed base 104 at the base of the Y-shaped portion 110. The mounting block 540 essentially takes the form of a modified channel section having a bottom 541 and sides 542 and short end walls 543, 543. A bar 544 is press fitted into holes in the sides 542, 542 and is positioned near one end of the mounting block 540. Slightly forward of the bar 544 there is an intermediate transverse wall 545 having a height slightly less than the height of the cross bar 544. Wall 545 cooperates with the upwardly ramped forwardly presenting surfaces 511a and 512a, 512a of the centermost latch finger 511 and outer latch fingers 512, 512, respectively, such that forward movement of the mule 450 causes these upwardly ramped forwardly presenting surfaces 511a and 512a, 512a to ride up the wall 545 and to latch over the bar 544. Referring to FIGS. 15 and 16, it will be seen that the distance between the radiused hook portion 511b of the centermost latch finger 511 and the axis of rotation of the sleeve 530 is slightly greater than the distance between the hook portions 512b, 512 b of the latch fingers 512, 512 and the axis of rotation of the sleeve 530. This allows the centermost latch finger 511 to initially latch the mule 450 to the bed 100, while further advancement of the mule 450 towards the bed 100 causes the outer latch fingers 512, 512 to then latch over the bar 544.

If the bed 100 is not loaded with a patient, the upwardly directed force of the gas springs 503, 503 acting upon bed base 110 can cause the bed base 110 to rise upwardly slightly. This slight upward movement of the bed base 110 requires a slightly longer latch finger, i.e., the centermost latch finger 511, to successfully latch the bed 100 to the mule 450, but when the bed is loaded up with a patient after the centermost latch finger 511 is latched over the bar 544 there is a slight amount of play between the bar 544 and the radiused hook portion 511b (FIG. 16). Accordingly, the outer latch fingers 512, 512 act as secondary latching devices such that all play is taken out of the connection between the mule 450 and the bed 100 after a patient is placed atop the bed 100 and thus loading the bed 100. In addition, the centermost latch finger 511 acts as a safety catch. This is because of the fact that when the rearwardly projecting handles 533 are depressed downwardly (FIG. 17) (either purposefully or inadvertently), thus pivoting the outer latch fingers 512, 512 off of the bar 544, there is a slight rotational delay between when these outer latch fingers 512, 512 disengage the bar 544 and when the centermost latch finger 511 disengages the latch bar, due to the cross pin 137 catching upon the upper surfaces of the outermost latch fingers 512, 512 at which time continued upward rotation of the outer latch fingers 512, 512 causes upward rotation of the centermost latch finger 511 and hence disconnection of the finger 511 from the crossbar 544.

To maintain the latching fingers 511 and 512, 512 in an approximately horizontally attitude, tension springs 550, 550 have upper ends connected to the crossbar 532 and lower ends indirectly connected to the upper fork supports 461, 461. A stop pin 551 is press fitted through the supports 461, 461 and serves to limit downward rotation of the latch fingers 511 and 512, 512, under the force of the springs 550, 550.

Figure 20:
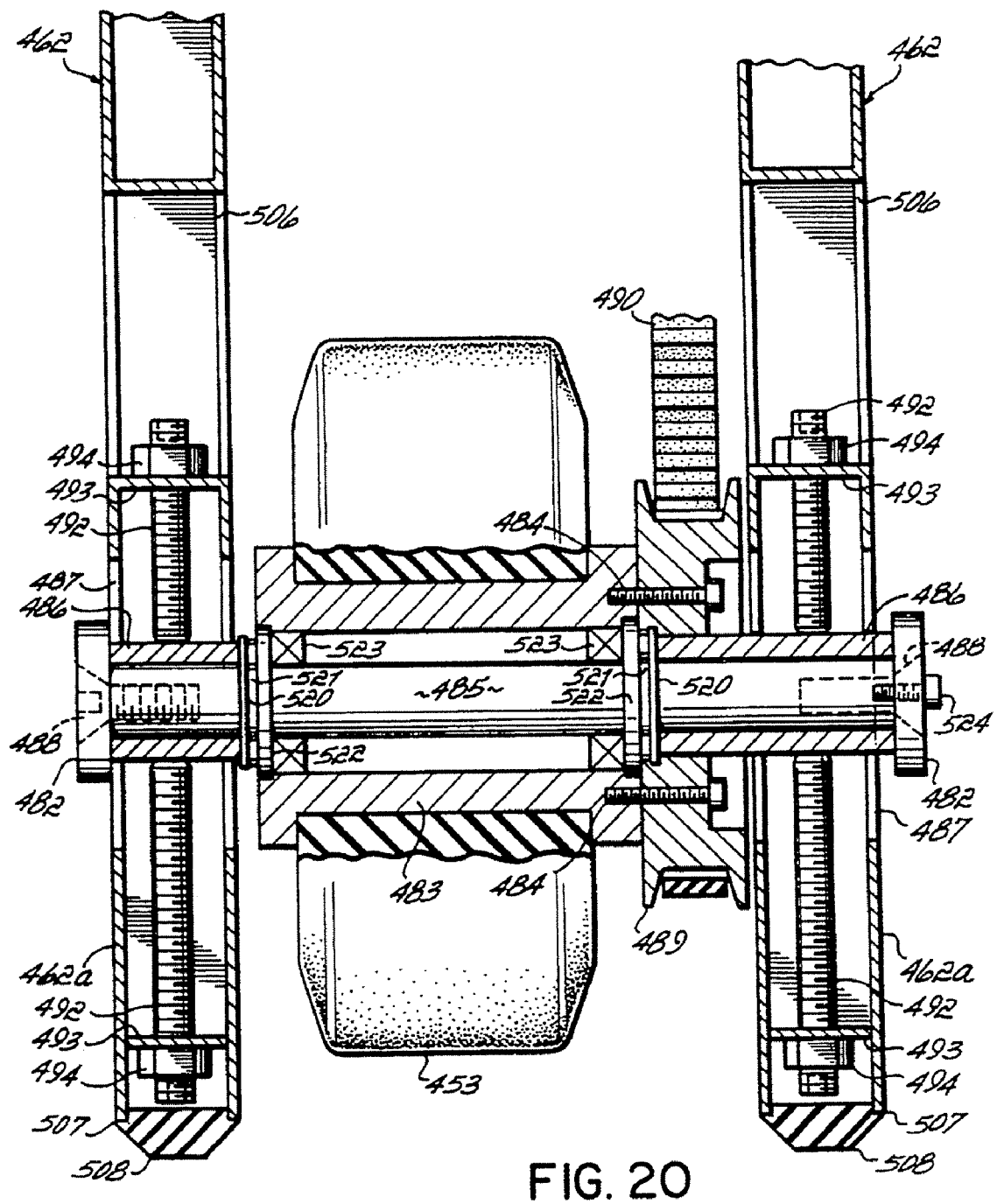
FIG. 20 is a view taken along line 20-20 of FIG. 19.

Referring to FIGS. 18 and 20, outwardly projecting nylon wedges 508, 508 inserted onto each end 461b of each support 461 guide the latching mechanism 510 onto the block 540, the wedges 508 directing the upper fork supports 461, 461 to the outer sides of the block 540. Initial entry of the mule 450 into the outspread arms 112, 112 of the bed base 110 is facilitated through the use of nylon shoulder wedges 555, 555, one of which is mounted at either end of the transversely oriented beam 451c of the mule base 451.

Referring back to FIG. 12, an on/off key 570 is provided for powering up the mule 450. An electronic fuel gauge 571 monitors the battery life in batteries 476, 476. The aforementioned joy stick control 457 is electrically connected to a pulse modulation controller circuit board 575 which is in turn electrically connected to the motor/gear box 477, and employs current pulsing technology to control the velocity of the motor 477 via the joy stick 457. A battery recharger 576 (FIG. 13) is included on board for recharging the batteries 476, 476.

A cord 572 is electrically connected to the recharger 576 and is adapted to be connected to an AC wall outlet for charging the batteries. When not in use, the cord 572 is wrapped about a pair of cord holders 573, 573 which are attached to one of the handles 454, 454. An amp meter 574 is viewable through the cover 458 for monitoring charge of the batteries 476, 476 during recharging.

Mule 450 of the present disclosure could be utilized to move other objects in a hospital setting or otherwise as well. It could be used as a motorized transport for care carts, for example, or any other piece of medical equipment, or any rollable object, which has a base defining an opening into which the mule could dock. Accordingly, the mule invention is not to be limited only to motorized transport of hospital beds.

Those skilled in the art will readily recognize numerous adaptations and modifications which can be made to the present invention and which will result in an improved combination nestable mobile ventilator, critical care bed, nestable care cart and nestable motorized transport, yet all of which will be within the spirit and scope of the present invention as defined by the following claims. Accordingly, the invention is to be limited only by the appended claims and their equivalents.

What is claimed is:

1. A patient support apparatus comprising:
   a patient support frame;
   a plurality of casters; and
   a powered transport device including at least one wheel and a motor, the powered transport device being positioned to lift at least a portion of the patient support frame and power movement of the patient support frame along the floor wherein the wheel of the powered transport device is configured to move between first and second positions relative to the patient support frame, the portion of the patient support frame being at a first height above a floor when the wheel is in the first position, the portion of the patient support frame being at a second height when the wheel is in the second position, the second height being greater than the first height.

2. The patient support apparatus of claim 1, wherein the plurality of casters includes at least four casters that are in contact with the floor when the wheel is in the first position.

3. The patient support apparatus of claim 1, wherein movement of the powered transport device between the first and second positions is provided by manual power.

4. The patient support apparatus of claim 1, wherein the wheel is in contact with the floor when the wheel is in the first and second positions.

5. The patient support apparatus of claim 1, wherein the powered transport device is spaced apart from the patient support frame when the wheel is in the second position.

6. The patient support apparatus of claim 1, wherein the patient support frame applies at least 400 Newtons force to the powered transport device.

7. A patient support apparatus comprising:
   a patient support including a patient support frame, a first pair of casters, and a second pair of casters longitudinally spaced apart from the first pair of casters, the patient support having a longitudinal center of gravity and a longitudinal midpoint positioned equidistant between head and foot ends of the patient support, and
   a powered transport device configured to power movement of the patient support along the floor, the powered transport device including a wheel positioned to engage the floor to move the patient support relative to the floor and a motor to power movement of the wheel, the wheel being positioned longitudinally closer to the longitudinal midpoint of the patient support than to the first pair of casters, and the wheel being longitudinally spaced apart from the longitudinal center of gravity of the patient support wherein the powered transport apparatus is configured to lift a portion of the patient support frame from a first height relative to the floor to a second height relative to the floor, the second height being greater than the first height.

8. The patient support apparatus of claim 7, wherein the combined longitudinal center of gravity of the powered transport device and the patient support is positioned between the wheel of the powered transport device and the head end of the patient support.

9. The patient support apparatus of claim 7, wherein the first pair of casters and the second pair of casters cooperate to define a caster footprint, and the wheel is positioned within the caster footprint.

10. A patient support apparatus comprising:
    a patient support including a patient support frame, a first pair of casters, and a second pair of casters longitudinally spaced apart from the first pair of casters, the patient support having a longitudinal center of gravity and a longitudinal midpoint positioned equidistant between head and foot ends of the patient support;
    a powered transport device configured to power movement of the patient support along the floor, the powered transport device including a wheel positioned to engage the floor to move the patient support relative to the floor and a motor to power movement of the wheel, the wheel being positioned longitudinally closer to the longitudinal midpoint of the patient support than to the first pair of casters, and the wheel being longitudinally spaced apart from the longitudinal center of gravity of the patient support; and
    a care cart dockable with the patient support, the care cart being configured to support patient care equipment, the wheel of the powered transport device being positioned approximate at the combined longitudinal center of gravity of patient support and care cart.

11. A patient support apparatus comprising:
    a patient support including a patient support frame, a plurality of casters, and a longitudinal center of gravity;
    a handle apparatus positioned adjacent to an end of the patient support to facilitate movement of the patient support;
    a wheel positioned to engage the floor at a position longitudinally between the handle apparatus and the longitudinal center of gravity of the patient support;
    a transport frame configured to couple the wheel to the patient support, the transport frame being coupled to the patient support frame at a location longitudinally spaced-apart from the plurality of casters; and
    a motor coupled to the wheel to power rotation of the wheel.

12. The patient support apparatus of claim 11, wherein the handle apparatus comprises a first vertically extending portion.

13. The patient support apparatus of claim 12, wherein the handle apparatus comprises a second vertically extending portion.

14. The patient support apparatus of claim 13, wherein the handle apparatus comprises a support coupled to the first vertically extending portion and to the second vertically extending portion.

15. The patient support apparatus of claim 14, wherein the first and second vertically extending portions are positioned adjacent a head end of the patient support.

16. The patient support apparatus of claim 11, further comprising a control in communication with the motor to control the velocity of the motor.

17. The patient support apparatus of claim 16, wherein the control is positioned laterally between the first and second vertically extending portions.

18. The patient support apparatus of claim 17, further comprising a controller circuit board electrically coupled to the control to receive an input signal therefrom and electrically coupled to the motor to send an output signal to the motor based on the input signal from the control.

19. The patient support apparatus of claim 11, further comprising a cord to provide electric power for the motor and a cord holder defining a recess to receive the cord during storage.

20. The patient support apparatus of claim 19, wherein the cord holder is coupled to at least one of the first and second vertically extending portions.

* * * * *